US010561712B2

(12) United States Patent
Lu et al.

(10) Patent No.: US 10,561,712 B2
(45) Date of Patent: Feb. 18, 2020

(54) TREATMENT OF CANCER AND INHIBITION OF METASTASIS USING HEMOGLOBIN BETA SUBUNIT

(71) Applicants: UNIVERSITY OF MARYLAND, BALTIMORE, Baltimore, MD (US); RAMOT AT TEL-AVIV UNIVERSITY LTD., Tel Aviv (IL)

(72) Inventors: Wuyuan Lu, Ellicott City, MD (US); Issac Witz, Ness Ziona (IL); Shelly Maman, Tel Aviv (IL)

(73) Assignees: UNIVERSITY OF MARYLAND, BALTIMORE, Baltimore, MD (US); RAMOT AT TEL AVIV UNIVERSITY LTD., Tel Aviv (IL)

( * ) Notice: Subject to any disclaimer, the term of this patent is extended or adjusted under 35 U.S.C. 154(b) by 85 days.

(21) Appl. No.: 15/312,928

(22) PCT Filed: May 21, 2015

(86) PCT No.: PCT/US2015/031996
§ 371 (c)(1),
(2) Date: Jun. 9, 2017

(87) PCT Pub. No.: WO2015/179657
PCT Pub. Date: Nov. 26, 2015

(65) Prior Publication Data
US 2017/0304410 A1 Oct. 26, 2017

Related U.S. Application Data

(60) Provisional application No. 62/095,413, filed on Dec. 22, 2014, provisional application No. 62/001,911, filed on May 22, 2014.

(51) Int. Cl.
| A61K 38/10 | (2006.01) |
| A61K 38/42 | (2006.01) |
| C07K 7/08 | (2006.01) |
| C07K 14/805 | (2006.01) |
| G01N 33/574 | (2006.01) |
| G01N 33/72 | (2006.01) |
| A61K 38/17 | (2006.01) |
| C12N 5/09 | (2010.01) |
| G01N 30/22 | (2006.01) |
| G01N 30/72 | (2006.01) |
| G01N 30/88 | (2006.01) |
| G01N 33/53 | (2006.01) |
| A61K 38/16 | (2006.01) |
| G01N 33/68 | (2006.01) |

(52) U.S. Cl.
CPC ............. *A61K 38/42* (2013.01); *A61K 38/10* (2013.01); *A61K 38/1709* (2013.01); *C12N 5/0693* (2013.01); *G01N 30/22* (2013.01); *G01N 30/72* (2013.01); *G01N 30/88* (2013.01); *G01N 33/53* (2013.01); *G01N 33/57488* (2013.01); *G01N 33/721* (2013.01); *A61K 38/16* (2013.01); *G01N 33/68* (2013.01); *G01N 2030/8813* (2013.01)

(58) Field of Classification Search
CPC .... A61K 38/10; A61K 38/16; A61K 38/1709; A61K 38/42; C07K 7/08; C07K 14/00; C07K 14/47; C07K 14/4717; C07K 14/805
See application file for complete search history.

(56) References Cited

U.S. PATENT DOCUMENTS

| 5,563,254 A | * | 10/1996 | Hoffman | C07K 14/805 435/69.5 |
| 2008/0004222 A1 | * | 1/2008 | Henkin | A61K 31/19 514/1.3 |
| 2010/0281003 A1 | * | 11/2010 | Jochim | G06F 19/16 707/692 |
| 2011/0319332 A1 | * | 12/2011 | Wong | A61K 38/42 514/15.3 |
| 2016/0184404 A1 | * | 6/2016 | Heini | A61K 38/42 514/13.5 |

FOREIGN PATENT DOCUMENTS

WO 2013/074820 5/2013

OTHER PUBLICATIONS

Capulli et at, "Increased Expression of a Set of Genes Enriched in Oxygen Binding Function Discloses a Predisposition of Breast Cancer Bone Metastases to Generate Metastasis Spread in Multiple Organs", Journal of Bone and Mineral Research, 27(11): 2387-2398 (2012).
Streckfus et al., "Salivary Protein Profiles among HER2/neu-Receptor-Positive and -Negative Breast Cancer Patients: Support for Using Salivary Protein Profiles for Modeling Breast Cancer Progression", Journal of Oncology, 2012: 1-9 (2012).
Liu et al., "Effect of Chronic Intermittent Hypoxia on Biological Behavior and Hypoxia-Associated Gene Expression in Lung Cancer Cells", Journal of Cellular Biochemistry, 111(3): 554-563 (2010).

(Continued)

*Primary Examiner* — Jeffrey E. Russel
(74) *Attorney, Agent, or Firm* — Wenderoth, Lind & Ponack, L.L.P.

(57) ABSTRACT

The beta 2 subunit of mouse hemoglobin (HBB2) has been identified as soluble factor from mouse lungs that exhibits cytostatic/cytotoxic activity against neuroblastoma lung micrometastases. The beta subunit of human hemoglobin (HBB) has been found to have similar activity. Methods of using these proteins and fragments thereof in the treatment of cancer and inhibition of metastasis are provided, along with methods of screening a subject for micrometastases by detecting HBB in a biological sample.

16 Claims, 17 Drawing Sheets
Specification includes a Sequence Listing.

(56) References Cited

OTHER PUBLICATIONS

Maman et al., "A new lung-derived factor inhibits neuroblastoma lung metastasis by inducing cancer cell dormancy", 15th International Biennial Congress of the Metastasis Research Society, Heidelberg, Germany, p. 181(B4) (2014).
International Search Report and Written Opinion of the International Searching Authority, dated Aug. 5, 2015, in corresponding International Application No. PCT/US2015/031996.

* cited by examiner

VHLTPEEKSAVTALWGKVNVDEVGGEALGRL
LVVYPWTQRFFESFGDLSTPDAVMGNPKVK
AHGKKVLGAFSDGLAHLDNLKGTFATLSELH
CDKLHVDPENFRLLGNVLVCVLAHHFGKEFT
PPVQAAYQKVVAGVANALAHKYH

↓

Mouse hemoglobin subunit beta (HBB2)

N

VHLTPEEKSAVTALWGKVN
VDEVGGEALGRLLVVYPWT
QRFFESFGDLSTPDAVM
_____
GNPKVKAHGKKVLGAFSD
GLAHLDNLKGTFATLSELH
C CDKLHVDPENFRLLGNVLV
CVLAHHFGKEFTPPVQAAY
QKVVAGVANALAHKYH

A.

B.

Days after tumor cell inoculation

A.

B.

TREATMENT OF CANCER AND INHIBITION OF METASTASIS USING HEMOGLOBIN BETA SUBUNIT

STATEMENT OF FEDERALLY SPONSORED RESEARCH AND DEVELOPMENT

This invention was made with government support under Grant No. A1072732 awarded by the National Institutes of Health. The government has certain rights in the invention.

SEQUENCE LISTING

A sequence listing in electronic (ASCII text file) format is filed with this application and incorporated herein by reference. The name of the ASCII text file is "62843_sequence_listing_ST25_1522647.txt"; the file was created on May 21, 2015; the size of the file is 10 KB.

BACKGROUND OF THE INVENTION

Metastasis is the major cause of cancer-related deaths (Gupta et al., 2006). Metastatic disease may develop years or even decades after successful treatment of the primary tumor (Aguirre-Ghiso et al., 2007; Pantel et al., 2004). This prolonged latency phase occurring between treatment and disease progression is often due to tumor dormancy (Aguirre-Ghiso et al., 2007), a stage in which residual disease is present but not clinically apparent. Tumor dormancy is caused either by cell cycle arrest (Chambers et al., 2002; Townson et al., 2006) or by a balance between proliferation and cell death (Holmgren et al., 1995). Tumor progression to late relapse and frank metastasis is often due to the awakening of dormant micrometastases (Chambers et al., 2002; Pantel et al., 2007; Wikman et al., 2008).

The mechanisms that sustain dormancy and those regulating the transition from dormancy to progressive disease from micrometastases remain widely unknown (Aguirre-Ghiso et al., 2007). However, the microenvironment is thought to play a critical role in tumor growth and progression (Joyce et al., 2009; Kim et al., 2011; Witz et al., 2008; Witz et al., 2008; Witz et al., 2006) and accumulating evidence suggests that the mechanisms governing tumor dormancy and metastatic recurrence are largely regulated by the microenvironment of the distant organ in which micrometastases are present (Klein-Goldberg et al., 2014; Maman et al., 2013b; Paez et al., 2012; Wikman et al., 2008).

A notable example is neuroblastoma, the most common extracranial solid tumor in children. Despite intensive treatment regimens, 60% to 70% of children with high-risk disease will ultimately experience relapse due to the presence of neuroblastoma micrometastasis (Smith et al., 2010). Since cure after relapse of high-risk disease is extremely rare, it is a necessity to identify novel and reliable modalities for the inhibition and elimination of neuroblastoma micrometastases.

Using a xenotransplant system (Nevo et al., 2008), it was reported that human neuroblastoma cells inoculated orthotopically into the adrenal gland of nude mice migrate to the lung and form dormant micrometastases (MicroNB) (Edry Botzer et al., 2011). These dormant micrometastases persist for long periods of time without forming overt metastasis. This situation is consistent with the observation that lung metastasis in neuroblastoma patients is a relatively late event in the progression of this disease (Cowie et al., 1997; Kammen et al., 2001). The state of dormancy of the micrometastatic cells is lung-specific: MicroNB cells harvested from lungs proliferated in culture and produced local tumors when inoculated into the adrenal gland of nude mice, indicating that once removed from the restraining lung microenvironment they were able to propagate (Edry Botzer et al., 2011).

Based on these findings, it was postulated that neuroblastoma lung metastases are regulated by the lung microenvironment. Specifically, it was hypothesized that the MicroNB cells residing in the lungs are dormant at this site because of proliferation-restraining functions of the lung microenvironment. This hypothesis was confirmed by a showing that lung-derived factors significantly reduced the viability of MicroNB cells by up-regulating the expression of pro-apoptotic genes, inducing cell cycle arrest, and decreasing ERK and FAK phosphorylation in these cells (Maman et al., 2013).

The identification of specific factors that maintain dormant micrometastases or that trigger active metastatic growth from micrometastases will be important in the development of new means for detecting the presence of micrometastases and for treating and/or preventing them. The present invention is directed to these and other important goals.

BRIEF SUMMARY

As described in detail below, the inventors of the present application found a soluble factor from normal mouse lungs that exhibits cytostatic/cytotoxic activity against neuroblastoma metastases and micrometastases to distant organs (such as lung, bone marrow, liver, and spleen), as well as several other cancers, such as breast, cervical, prostate, skin (melanoma) and lung carcinoma. The molecule was purified and identified as the beta 2 subunit of mouse hemoglobin (HBB2). Purified human hemoglobin beta subunit (HBB), which shares 80% sequence identity to mouse HBB2, was found to have a comparable cytostatic/cytotoxic effect on neuroblastoma cells, whereas the alpha subunit of human hemoglobin was inactive.

The inhibitory activity of HBB was found in the carboxy-terminal part of the protein in a specific amino acid sequence (ENFRLLGNVLVCVLA, termed HBB11p; SEQ ID NO:5). Treatment with this short inhibitory peptide significantly inhibited local neuroblastoma tumor growth, and both lung and bone marrow metastasis, indicating its potential to serve as a new anticancer drug.

HBB2 expression is significantly elevated in the serum and organs of mice harboring neuroblastoma micrometastases, indicating that HBB can serve as a biomarker for predicting tumor progression.

Thus, and in a first aspect, the present invention is directed to methods of screening a subject for micrometastases comprising (a) obtaining a biological sample from a subject, (b) determining the amount of an HBB peptide in the sample, and (c) comparing to amount determined in (b) with a reference amount.

In one particular aspect, when the amount determined in (b) is more than the reference amount, the subject is diagnosed as having micrometastases. In another particular aspect, when the amount determined in (b) is the same as or less than the reference amount, the subject is diagnosed as being free of micrometastases.

In this first aspect, the biological sample may be, but is not limited to, blood, serum and sputum.

In this first aspect, the HBB peptide may be, but is not limited to, HBB (i.e., human hemoglobin beta subunit).

In this first aspect, the amount of an HBB peptide in the biological sample may be determined by means that include, but are not limited to, western blot, dot blot, slot blot, ELISA, RP-HPLC, LC-MS and LC-MS/MS.

In this first aspect, the micrometastases may be, but are not limited to, breast, cervical, prostate, kidney, lung, skin, ovarian, pancreatic, prostate, rectal, stomach, thyroid, cervical, and uterine cancer, or cancer of the nervous system, in origin. In particular, the micrometastases may be neuroblastomal (cancer of the nervous system) in origin.

In a second aspect, the present invention is directed to methods of treating a subject having cancer comprising administering an effective amount of an HBB peptide to a subject having cancer.

The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

In a non-limiting example, the method is one of treating a subject having neuroblastoma comprising administering an effective amount of an HBB peptide to a subject having neuroblastoma.

In a third aspect, the present invention is directed to methods of inhibiting development of cancer in a subject at risk of developing cancer comprising administering an effective amount of an HBB peptide to a subject at risk of developing cancer.

The subject at risk of developing cancer may be a subject that was previously treated for cancer or neuroblastoma. The subject at risk of developing cancer may be a subject in which cancer or neuroblastoma was previously cured.

The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

In a non-limiting example, the method is one inhibiting development of neuroblastoma in a subject at risk of developing neuroblastoma comprising administering an effective amount of an HBB peptide to a subject at risk of developing neuroblastoma.

In a fourth aspect, the present invention is directed to methods of inhibiting metastasis of cancer in a subject having cancer comprising administering an effective amount of an HBB peptide to a subject having cancer.

The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

In a non-limiting example, the method is one inhibiting metastasis of neuroblastoma in a subject having neuroblastoma comprising administering an effective amount of an HBB peptide to a subject having neuroblastoma.

In a fifth aspect, the present invention is directed to pharmaceutical compositions comprising one or more HBB peptides and a pharmaceutically acceptable carrier.

In relevant aspects of the invention, the HBB peptide is one that is selected from the group consisting of (a) mouse HBB2, (b) human HBB, (c) a peptide comprising HBB11p (SEQ ID NO:5), (d) a peptide consisting of HBB11p, e) a variant of any one of (a) through (d) having 10 or fewer amino acid changes, and (f) functional derivatives of (a) through (e).

In relevant aspects of the invention, the HBB peptide may be administered to the subject as a pharmaceutical composition comprising an HBB peptide and a carrier.

In a sixth aspect, the present invention is directed to the use of an HBB peptide in a method of treating a subject having cancer. In a non-limiting example, an effective amount of an HBB peptide is administered to a subject having cancer.

The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

In a non-limiting example, the HBB peptide is used in a method of treating a subject having neuroblastoma, wherein an effective amount of an HBB peptide is administered to a subject having neuroblastoma.

In a seventh aspect, the present invention is directed to the use of an HBB peptide in a method of inhibiting development of cancer in a subject at risk of developing cancer. In a non-limiting example, an effective amount of an HBB peptide is administered to a subject at risk of developing cancer.

The subject at risk of developing cancer may be a subject that was previously treated for cancer or neuroblastoma. The subject at risk of developing cancer may be a subject in which cancer or neuroblastoma was previously cured.

The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

In a non-limiting example, the HBB peptide is used in a method of inhibiting development of neuroblastoma in a subject at risk of developing neuroblastoma, wherein an effective amount of an HBB peptide is administered to a subject at risk of developing neuroblastoma.

In an eighth aspect, the present invention is directed to use of an HBB peptide in a method of inhibiting metastasis of cancer in a subject having cancer. In a non-limiting example, an effective amount of an HBB peptide is administered to a subject having cancer.

The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

In a non-limiting example, the HBB peptide is used in a method of inhibiting metastasis of neuroblastoma in a subject having neuroblastoma, wherein an effective amount of an HBB peptide is administered to a subject having neuroblastoma.

In a ninth aspect, the present invention is directed to the use of an HBB peptide for the manufacture of a medicament for treating cancer in a subject. The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma. In a non-limiting example, the HBB peptide is used for the manufacture of a medicament for treating neuroblastoma in a subject.

In a tenth aspect, the present invention is directed to the use of an HBB peptide for the manufacture of a medicament for inhibiting development of cancer in a subject at risk of developing cancer. The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma. In a non-limiting example, the HBB peptide is used for the manufacture of a medicament for inhibiting development of neuroblastoma in a subject at risk of developing neuroblastoma.

In an eleventh aspect, the present invention is directed to the use of an HBB peptide for the manufacture of a medicament for inhibiting metastasis of cancer in a subject having cancer. The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma. In a non-limiting example, the HBB peptide is used for the manufacture of a medicament for inhibiting metastasis of cancer in a subject having cancer.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1A: Normal mouse lungs (ConLung) were harvested, minced and filtered, and soluble factors were collected. FIG. 1B: MTS-based viability assay indicated that dialyzed (3500 MW Da cutoff) lung-derived factors inhibited cell viability to the same extent as non-dialyzed lung-derived factors. FIG. 1C: HPLC separation of dialyzed lung-derived factors resulted in 4 distinctive peaks. FIG. 1D: MTS-based viability assay revealed that peak no. 4 inhibited cell viability. FIG. 1E: HPLC purification of peak no. 4 resulted in one peak. *p<0.05, p<0.01, *p<0.005.

FIG. 2A: Mass spec analysis of the HPLC-separated peak no. 4 indicated that the peak harbored a single protein of a MW of 15824.5 Da. FIG. 2B: Sequence analysis by LC-MS/MS coupled with tryptic digestion of the inhibitory peak no. 4 revealed a 147 amino acid sequence (SEQ ID NO:1). Database search in the International Protein Index (IPI) revealed a 100% identity to the mouse beta subunit of hemoglobin (HBB2). FIG. 2C: HBB2 was verified as the inhibitory lung factor when the addition of a specific anti-mouse HBB2 antibody blocked the inhibitory activity of lung-derived factors incubated with MicroNB and MacroNB cells.*p<0.05, p<0.01, *p<0.005.

FIG. 3A: HPLC separation of native human hemoglobin resulted in the isolation of the beta subunit of a MW of 15867 Da. FIG. 3B: Structure prediction of human HBB by 1-TASSER tool revealed a helical structure. FIG. 3C: Circular dichroism analysis of human hemoglobin (HB), hemoglobin subunit alpha (HBA) and subunit beta (HBB) indicated a helical structure for all three proteins. FIG. 3D: MTS-based viability assay indicated that human HBB inhibits the viability of MicroNB and MacroNB cells. HBA did not influence cell viability. FIG. 3E: MTS-based viability assay indicated that human HBB inhibits the viability of MCF-7 breast carcinoma cells as well. The whole human hemoglobin protein inhibited cell viability as well but not to the same extent as HBB. *p<O.OS, p<0.01, *p<0.005, ****p<0.001.

FIG. 4A: Whole cell lysates of MicroNB and MacroNB cells incubated with human HBB were subjected to western blot analysis and immunostaining. ERK1/2 phosphorylation was calculated in reference to total ERK2, as measured by densitometry. FIG. 4B: Cell-cycle analysis was performed using flow cytometry to examine the percentage of cells in G0-G1 phase. FIG. 4C: Whole cell lysates of MicroNB and MacroNB cells incubated with human HBB were subjected to western blot analysis and immunostaining. Cyclin D1 expression was calculated in reference to beta-tubulin. *p<0.05, p<0.01, *p<0.005, ****p<0.001.

FIG. 5A: Cleavage of human HBB protein after the amino acid methionine using CNBr resulted in N- and C-terminal fragments (SEQ ID NOs:3 and 4). FIG. 5B: MTS-viability assay revealed that most of the inhibitory activity of human HBB is in the C-terminal part of the protein. FIG. 5C: MTS-based viability assay indicated that peptide 11 of human HBB inhibited the viability of MicroNB cells to a greater extent than human HBB. *p<0.05, p<0.01, *p<0.005.

FIG. 8A: Mice were orthotopically inoculated to the adrenal gland with neuroblastoma micrometastases. Fourteen days post inoculation, mice were intranasally treated with HBB11p ("Metox") or with a scrambled Metox peptide (control group), once a week for 8 weeks. Mice were monitored weekly for tumor volume. At the end of the experiment, local tumors were weighed and organs were harvested and examined for the presence of human neuroblastoma cells and for mHBB2 expression using real time PCR. FIG. 8B: Volume measurements of local tumors of mice treated with Metox or scrambled-Metox. FIG. 8C: Mice treated with Metox or scrambled-Metox were photographed right before the extraction of local adrenal tumors. Local adrenal tumors were photographed as well. FIG. 8D: Local adrenal tumors were weighed right after extraction from mice. FIG. 8E: Real time PCR quantification of MicroNB cells in mouse lungs. FIG. 8F: Real time PCR quantification of MicroNB cells in mouse bone marrow. Data are means of mice in each group (n=24, 12 mice in each group)±SD. Significance was evaluated using Student's t-test. *p<0.05, p<0.01, *p<0.005, ****p<0.001.

DETAILED DESCRIPTION

Figure 1A:
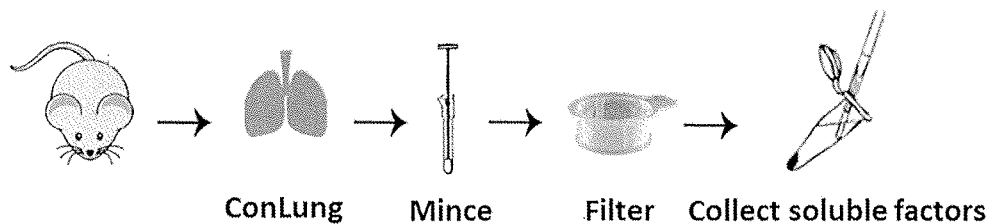
FIGS. 1A-1E. Isolation of an inhibitory lung factor.

The hypothesis underlying the present invention is that factors from the lung microenvironment restrain the proliferation of micrometastases from neuroblastoma and other cancers, thus inhibiting progression towards overt metastasis. In a previous study (Maman et al., 2013), the inventors demonstrated that indeed the microenvironment of the normal lung possesses the capacity to do so. Factors derived from normal mouse lungs significantly inhibited the viability of MicroNB cells, up-regulated apoptosis and down-regulated cell cycle progression genes, induced cell cycle arrest and apoptosis, up-regulated the expression of stem cell markers and decreased ERK and FAK phosphorylation in these cells. This microenvironment-mediated regulation of neuroblastoma cell viability supported the hypothesis that factors in the lung microenvironment kept the micrometastatic tumor cells in a state of dormancy and inhibited their propagation thereby preventing overt lung metastasis.

As reported herein, the inventors have now isolated a soluble factor from normal mouse lungs that exhibits cytostatic/cytotoxic activity against neuroblastoma lung metastases and micrometastases, namely the beta 2 subunit of mouse hemoglobin (HBB2). Along with its human counterpart (HBB), these hemoglobin beta subunits can be employed as anticancer drugs either alone or in combination with other drugs and/or cancer treatments. For example, an HBB peptide can be used alone or with other drugs to treat primary tumors, inhibit developments and/or growth of primary tumors, to treat minimal residual disease in cancer patients (e.g., in conjunction with surgery, chemotherapy, and/or radiation therapy), and/or to inhibit or block development and progression of metastatic cancer. HBB peptides can be derivatized to increase their half-life and/or bioavailability, and/or to improve their targeting to cancerous tissue.

Truncation studies on the beta chain of human hemoglobin (HBB) identified the amino acid sequence ENFRLLGNVLVCVLA (HBB11p; SEQ ID NO:5) as containing the anti-tumor/anti-metastatic activity of the larger protein, both in vivo and in vitro. This peptide, also designated Metox, can be used as an anti-tumor drug.

The identification of endogenous HBB as a factor that inhibits micrometastatic neuroblastoma cells and perhaps other metastasizing cells indicates that the arsenal of innate resistance mechanisms may contain factors with unrelated physiological functions. Such endogenous factors may take part in regulated cancer recurrence and can be employed to develop novel therapies to treat and prevent cancer metastasis and for the treatment of residual disease.

Moreover, because the beta subunit of murine hemoglobin (HBB2) is expressed by lung cells and it is up-regulated in nude mice bearing human neuroblastoma xenografts, HBB2 and HBB can be used as biomarkers for disease.

HBB Peptides

For the sake of convenience, the proteins and peptides that may be used in the various aspects of the present invention are termed "HBB peptides" herein. The proteins and peptides include (a) the beta subunit of mouse hemoglobin (HBB2; SEQ ID NO:1), (b) the beta subunit of human hemoglobin (HBB; SEQ ID NO:2), (c) the 91 amino acid C-terminal fragment of HBB set forth in SEQ ID NO:4 (termed "HBB91"), (d) the 15 amino acid fragment of HBB set forth in SEQ ID NO:5 (termed "HBB11p" and "Metox"), (e) functional fragments of HBB2, HBB and HBB91, (f) functional variants of HBB2, HBB, HBB91, HBB11p and the functional fragments, and (g) functional derivatives of each of the proteins and peptides of (a) through (f).

As used herein, "functional fragments" are those having at least about 10, 11, 12, 13, 14, 15, 16, 17, 18, 19, 20, 21, 22, 23, 24, 25, 26, 27, 28, 29, 30 or more contiguous amino acids of HBB2, HBB or HBB91. Each of the functional fragments retains the activity of the protein or peptide upon which a particular fragment is based.

As used herein, "functional variants" are those having at least about 90, 91, 92, 93, 94, 95, 96, 97, 98, or 99% sequence homology to the protein or peptide upon which they are based, or that have X or fewer amino acids changes, where X is 20, 19, 18, 17, 16, 15, 14, 13, 12, 11, 10, 9, 8, 7, 6, 5, 4, 3, 2 or 1, in comparison to the protein or peptide upon which they are based. The changes are independently selected from additions, deletions and substitutions. The substitutions may be conservative or non-conservative amino acid substitutions. Each of the functional variants retains the activity of the protein or peptide upon which a particular variant is based.

As used herein, "functional derivatives" include, but are not limited to, proteins and peptides comprising one or more L-amino acids, proteins and peptides comprising one or more D-amino acids, proteins and peptides comprising one or more synthetic amino acids, cyclized peptides, peptides with derivatized amino acids, chimeric peptides wherein an HBB peptide is fused to another peptide or polypeptide, HBB peptides fused to other chemical moieties, HBB peptides enclosed within liposomes or nanoparticles or hydrogels, and the like. Also included are (i) the D-enantiomer or inverso-peptide having the same sequence as the reference protein or peptide, but composed of D-amino acids and a mirror conformation; (ii) the retro-peptide, consisting of the same sequence of L amino acids but in reverse order; and (iii) the retro-inverso or D-retro-enantiomer peptide, consisting of D-amino acids in the reversed sequence. Each of the functional derivatives retains the activity of the protein or peptide upon which a particular derivative is based.

Pharmaceutical Formulations

The invention provides pharmaceutical formulations comprising one or more of the HBB peptides of the invention and a pharmaceutically acceptable carrier. Such formulations may be administered to a subject, such as a human. Suitable examples of carriers are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

Micrometastases

Metastasis is the spread of a cancer from its original location to other sites in the body, where secondary tumors are formed. These secondary tumors initially comprise such a small number of cells that there are very difficult to detect in a subject. At the stage when the secondary tumors are too small to be detected by convention means, the tumors are termed "micrometastases". As used herein, micrometastases are not limited to the cells of a particular tumor or cancer. However, in one aspect, the present invention encompasses micrometastases comprising neuroblastoma cells. Such micrometastases are termed "MicroNB".

Methods of Screening

The presence of micrometastases in the organs and systems of a subject is nearly impossible to detect due to their scarcity and the absence of detection methods.

Described herein is the first report that the expression level of HBB is elevated in organs harboring micrometastases and in the serum of micrometastases-bearing subjects. Accordingly, HBB peptides can serve as biomarkers for the presence of micrometastases, as well as predicting tumor progression. For example, HBB peptide levels in the serum of a subject can be measured to determine the presence of micrometastases. HBB peptide levels can also be used to indicate the efficacy of particular treatments, thereby guiding the choice of treatment regimens and decisions. In a general aspect, the invention includes methods of screening a subject for micrometastases comprising (a) obtaining a biological sample from a subject, (b) determining the amount of an HBB peptide in the sample, and (c) comparing to amount determined in (b) with a reference amount.

The micrometastases to be screened can be comprised of cells originating from any type of cancer, including breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the micrometastases are neuroblastomal in origin.

The characteristics of a subject to be screened are not limited and can include one that has not previously been diagnosed or suspected of having micrometastases, one that currently has micrometastases, or one that previously had micrometastases but was shown to be free of micrometastases.

The biological sample is as defined herein; an exemplary biological sample is serum.

The identity of the HBB peptide to be screened is as defined herein, but exemplary forms include native hemoglobin beta subunit, such as native human hemoglobin beta subunit (i.e., HBB).

The amount of HBB peptide may be determined by conventional means for either determining whether a particular protein is present in a biological sample and/or determining the amount of a particular protein in a biological sample. Such means include western blot analysis, dot- or slot-blot analysis, and enzyme-linked immunosorbent assays (ELISA). Additional means include RP-HPLC (reversed-phase high-performance liquid chromatography), LC-MS (liquid chromatography-mass spectrometry) and LC-MS/MS (liquid chromatography tandem mass spectrometry).

The reference amount of HBB peptide used in the present method is one determined from a subject or group of subject that has been previously characterized with respect to the presence and/or amount of micrometastases present in the subject or group of subject. A comparison using the reference amount permits one to determine whether micrometastases are present in the subject and the amount of micrometastases present in the subject. While not intending to be bound by theory, the higher the amount of HBB peptides determined to be present in the biological sample, the more likely it is that the subject has micrometastases.

In a particular example of this aspect of the invention, when the amount determined in (b) is more than the reference amount, the subject is diagnosed as having micrometastases. In another particular aspect, when the amount determined in (b) is the same as or less than the reference amount, the subject is diagnosed as being free of micrometastases.

Methods of Treatment and Inhibition

The invention is also directed to therapeutic uses for HBB peptides. As shown in the examples, HBB peptides can have cytostatic and cytotoxic effects on cancer cells. Thus, the HBB peptides, and pharmaceutical formulations comprising the peptides, can be used in methods of treating and inhibiting cancer in a subject.

In one aspect, the invention is directed to methods of treating a subject having cancer comprising administering an effective amount of an HBB peptide to the subject. In a non-limiting example, the cancer is neuroblastoma.

In a second aspect, the invention is directed to methods of inhibiting development of cancer in a subject at risk of developing cancer comprising administering an effective amount of an HBB peptide to a subject at risk of developing cancer. In a non-limiting example, the cancer is neuroblastoma.

In a third aspect, the invention is directed to methods of inhibiting metastasis of a cancer in a subject having cancer comprising administering an effective amount of an HBB peptide to a subject having cancer. In a non-limiting example, the cancer is neuroblastoma.

In first related aspect, the invention is directed to methods of inducing cytostasis in the cells of a cancer or tumor in a subject comprising administering an effective amount of an HBB peptide to the subject. In a non-limiting example, the cancer is neuroblastoma.

In second related aspect, the invention is directed to methods of inducing cytostasis in the cells of a cancer or tumor comprising contacting cells of a cancer or tumor with an effective amount of an HBB peptide. In a non-limiting example, the cancer is neuroblastoma.

In third related aspect, the invention is directed to methods of inducing cell cycle arrest in the cells of a cancer or tumor in a subject comprising administering an effective amount of an HBB peptide to the subject. In a non-limiting example, the cancer is neuroblastoma. In a non-limiting example, the cell cycle arrest is in the G0-G1 phase.

In fourth related aspect, the invention is directed to methods of inducing cell cycle arrest in the cells of a cancer or tumor comprising contacting cells of a cancer or tumor with an effective amount of an HBB peptide. In a non-limiting example, the cancer is neuroblastoma. In a non-limiting example, the cell cycle arrest is in the G0-G1 phase.

In each of these aspects of the invention related to methods of treatment and inhibition, the methods can be practiced using HBB peptides alone or practiced in conjunction with additional means for treating and inhibiting cancer in a subject. Such additional means will be well known to the skilled artisan and include, but are not limited to means such as anti-cancer chemotherapeutics and surgical removal of a tumor.

As used herein, the terms "treat", "treating" and "treatment" have their ordinary and customary meanings, and include one or more of complete or partial clearance of a tumor or cancer from a subject, reducing the size of a tumor in a subject, killing cells of a tumor or cancer in a subject, and ameliorating a symptom of cancer or a tumor in a subject. Treatment means clearing, reducing, killing or ameliorating by about 1% to about 100% versus a subject to which an HBB peptide has not been administered. Preferably, the clearing, reducing, killing or ameliorating is about 100%, about 99%, about 98%, about 97%, about 96%, about 95%, about 90%, about 80%, about 70%, about 60%, about 50%, about 40%, about 30%, about 20%, about 10%, about 5% or about 1%. The results of the treatment may be permanent or may continue for a period of days (such as 1, 2, 3, 4, 5, 6 or 7 days), weeks (such as 1, 2, 3 or 4 weeks), months (such as 1, 2, 3, 4, 5, 6 or more months) or years (such as 1, 2, 3, 4, 5, 6 or more years).

As used herein, the terms "inhibit", "inhibiting" and "inhibition" have their ordinary and customary meanings, and include one or more of, hindering, impeding, obstructing, deterring or restraining establishment of cancer or a tumor, development of cancer or a tumor, growth of cancer or a tumor and metastasis. Inhibition means hindering by about 1% to about 100% versus a subject to which an HBB peptide has not been administered. Preferably, the hindering is about 100%, about 99%, about 98%, about 97%, about 96%, about 95%, about 90%, about 80%, about 70%, about 60%, about 50%, about 40%, about 30%, about 20%, about 10%, about 5% or about 1%. The methods of inhibition may be practiced in a subject prior to, concurrent with, or after the onset of clinical symptoms of cancer or a tumor. Thus, the subject may have cancer or a tumor, or merely be susceptible to developing cancer or a tumor. The results of the inhibition may be permanent or may continue for a period of days (such as 1, 2, 3, 4, 5, 6 or 7 days), weeks (such as 1, 2, 3 or 4 weeks), months (such as 1, 2, 3, 4, 5, 6 or more months) or years (such as 1, 2, 3, 4, 5, 6 or more years).

The HBB peptides and formulations comprising HBB peptides may be administered to a subject using different schedules, depending on the particular aim or goal of the method; the age and size of the subject; and the general health of the subject, to name only a few factors to be considered. In general, the HBB peptides and formulations may be administered once, or twice, three times, four times, five times, six times or more, over a course of treatment or inhibition. The timing between each dose in a dosing schedule may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of HBB peptide may be administered in each dose of the dosing schedule, or the amounts in each dose may vary. The identity of the HBB peptide may also vary or remain the same in each dose in a dosing schedule.

In each of the methods of the present invention, an "effective amount" of an HBB peptide or pharmaceutical formulation comprising an HBB peptide is administered to a subject. The effective amount will vary between subjects. However, the effective amount is one that is sufficient to achieve the aim or goal of the method, whether inhibiting or treating. As an example, an effective amount of an HBB peptide used in the methods of the invention is typically between about 0.1 µg to about 10,000 µg of HBB peptide per kg of body weight of the subject to which the peptide is administered. An effective amount also includes between about 0.5 µg to about 5000 µg, between about 1 µg to about 500 µg, between about 10 µg to about 200 µg, between about 1 µg to about 800 µg, between about 10 µg to about 1000 µg, between about 50 µg to about 5000 µg, between about 50 µg to about 500 µg, between about 100 µg to about 1000 µg, between about 250 µg to about 2500 µg, between about 500 µg to about 2000 µg, between about 10 µg to about 800 µg, between about 10 µg to about 1000 µg, between about 1 µg to about 300 µg, and between about 10 µg to about 300 µg of HBB peptide per kg of body weight of the subject.

Appropriate doses and dosing schedules can readily be determined by techniques well known to those of ordinary skill in the art without undue experimentation. Such a determination will be based, in part, on the tolerability and efficacy of a particular dose.

Administration of the HBB peptide or formulation may be via any of the means commonly known in the art of peptide delivery. Such routes include intravenous, intraperitoneal, intramuscular, subcutaneous and intradermal routes of administration, as well as nasal application, by inhalation, ophthalmically, orally, rectally, vaginally, or by any other mode that results in the HBB peptide or formulation contacting mucosal tissues.

As used herein, the cancer and tumor are not limited and include, for example, breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

As used herein, the term "biological sample" includes tissues (e.g., tissues obtained during a biopsy, including the clean margins of the resected tissue), cells, biological fluids (e.g., blood, serum, plasma, saliva, sputum, sweat, urine) and isolates thereof, isolated from a subject, as well as tissues, cells and fluids present within a subject.

As used herein, the term "subject" is intended to mean an animal, such birds or mammals, including humans and animals of veterinary or agricultural importance, such as dogs, cats, horses, sheep, goats, and cattle.

A kit comprising the necessary components for practicing the methods disclosed herein is also within the purview of the present invention. The kit comprises one or more HBB peptides and instructions for use. In some aspects, the one or more HBB peptides are in a pharmaceutical formulation comprising the HBB peptides and a pharmaceutically acceptable carrier.

Uses of the HBB Peptides

In addition to the compositions and methods described herein, the present invention is also directed to uses for the HBB peptides in various (i) methods of treatment or inhibition and (ii) methods of manufacture.

For example, the invention is directed to the use of an HBB peptide in one or more methods of (i) treating a subject having cancer, (ii) inhibiting development of cancer in a subject at risk of developing cancer, and (iii) inhibiting metastasis of cancer in a subject having cancer. In non-limiting examples, an effective amount of an HBB peptide is administered to a subject in each of these uses.

In each of these uses, the cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

In a non-limiting example, the HBB peptide is used in a method of treating a subject having neuroblastoma, wherein an effective amount of an HBB peptide is administered to a subject having neuroblastoma.

In another non-limiting example, the HBB peptide is used in a method of inhibiting development of neuroblastoma in a subject at risk of developing neuroblastoma, wherein an effective amount of an HBB peptide is administered to a subject at risk of developing neuroblastoma.

In a further non-limiting example, the HBB peptide is used in a method of inhibiting metastasis of neuroblastoma in a subject having neuroblastoma, wherein an effective amount of an HBB peptide is administered to a subject having neuroblastoma.

When the use is one of inhibiting development of cancer in a subject at risk of developing cancer, the subject at risk of developing cancer may be a subject that was previously treated for cancer or neuroblastoma or the subject at risk of developing cancer may be a subject in which cancer or neuroblastoma was previously cured.

As suggested above, the invention is also directed to the use of an HBB peptide for the manufacture of a medicament for (i) treating cancer in a subject, inhibiting development of cancer in a subject at risk of developing cancer, and (iii) inhibiting metastasis of cancer in a subject having cancer. The cancer may be one or more of breast, cervical, colon, kidney, lung, skin (e.g., melanoma), ovarian, pancreatic, prostate, rectal, stomach, thyroid, cervical, and uterine cancer, and cancer of the nervous system (e.g., neuroblastoma). In one example, the cancer is neuroblastoma.

In a non-limiting example, the HBB peptide is used for the manufacture of a medicament for treating neuroblastoma in a subject.

In another non-limiting example, the HBB peptide is used for the manufacture of a medicament for inhibiting development of neuroblastoma in a subject at risk of developing neuroblastoma.

In a further non-limiting example, the HBB peptide is used for the manufacture of a medicament for inhibiting metastasis of cancer in a subject having cancer.

EXAMPLES

The eight examples provided further below each used the materials and methods detailed in the following paragraphs.

Cell Culture

The human neuroblastoma lung micrometastatic (MicroNB) and macrometastatic (MacroNB) variants were generated using a mouse model for human neuroblastoma metastasis (Nevo et al., 2008) from the parental cell lines MHH-NB11 (Pietsch et al., 1988) and SH-SY5Y (Biedler et al., 1978) as detailed here (Edry Botzer et al., 2011), and were maintained in culture as previously described (Nevo et al., 2008). The MicroNB and MacroNB variants were previously designated DisNB and MetNB, respectively (Edry Botzer et al., 2011). Authentication of MicroNB and MacroNB cells was performed by short tandem repeat analysis of DNA using the Type-it Microsatellite PCR Kit (Qiagen, Valencia, Calif.), for the genes published by the American Type Culture Collection (ATCC) (Manassas, Va.). The parental cell line MHH-NB11 was kindly provided by Dr. T. Pietsch (Department of Neuropathology, University of Bonn Medical Center, Bonn, Germany).

All cultures were periodically examined for *mycoplasma* contamination.

Animals

Male athymic nude mice (BALB/c background) were purchased from Harlan Laboratories Limited (Jerusalem, Israel) or from the Shanghai Laboratory Animal Center (Chinese Academy of Sciences, Shanghai, People's Republic of China). The mice were housed and maintained for approximately 4 weeks in laminar flow cabinets under specific pathogen-free conditions at the animal quarters of Tel Aviv University (Tel Aviv, Israel) or of Fudan University (Shanghai, People's Republic of China), in accordance with current regulations and standards of institutional animal care committees. Mice of 7-10 weeks old were used for experiments in accordance with institutional ethical guidelines.

Antibodies

Goat polyclonal anti-mouse Hemoglobin β (sc-31116; Santa Cruz Biotechnology Inc., Santa Cruz, Calif.), was used at a dilution of 1:1000 for immunoblotting, at a dilution of 1:50 for immunofluorescence of frozen sections and at a concentration of 1 µg/ml, 10 µg/ml or 100 µg/ml for neutralizing the inhibitory activity of lung-derived factors. Rabbit polyclonal anti-human ERK2 (C-14; Santa Cruz Biotechnology, Inc.), anti-human phosphorylated-ERK1/2 (R&D Systems, Minneapolis, Minn.), anti-human phosphorylated-p38 MAPK (Thr180/Tyr182) (D3F9; Cell Signaling, Massachusetts, USA), anti-human p38 MAPK (M0800; Sigma-Aldrich, St. Louis, Mo., USA), anti-human phosphorylated-TAK1 (Thr184/187) (9007; Cell Signaling) and anti-human TAK1 (4504S; Cell Signaling) were used at a dilution of 1:1000 for immunoblotting. Mouse monoclonal anti-human Cyclin D1 (DCS-6; Thermo Scientific, Cheshire, UK) and mouse monoclonal anti-human β-Tubulin (T4026; Sigma-Aldrich) were used at a dilution of 1:500 and 1:2000, respectively, for immunoblotting. Horseradish peroxidase (HRP)-conjugated donkey anti-goat, goat anti-mouse and goat anti-rabbit antibodies were used according to the manufacturer instructions (Jackson ImmunoResearch Laboratories, West Grove, Pa.) for immunoblotting. Fluorescein isothiocyanate (FITC)-conjugated donkey anti-goat IgG (Jackson Immuno Research Laboratories) was diluted 1:200 for immunofluorescence of frozen tissues.

In Vitro Viability Assays

Neuroblastoma cells were seeded ($3 \times 10^4$ per well) in a 96-well flat-bottomed tissue culture plate. After an incubation of 24 hr, cells were washed and incubated with the relevant factors (detailed in the following sections) diluted in starvation medium (RPMI-1640 containing 5% bovine serum albumin (BSA); Biological Industries, Kibbutz Beit Haemek, Israel; Sigma-Aldrich). Cell viability under normal conditions (starvation medium containing BSA) or after incubation with the relevant factors was monitored after 72 hr using an XTT (XTT cell proliferation kit; Biological Industries) or MTS-based (CellTiter 96® AQueous One Solution Cell Proliferation Assay; Promega) viability assays according to manufacturer instructions. Cells were also counted using the trypan-blue exclusion assay to verify the results obtained by XTT and MTS-based viability assays.

Preparation of Factors Derived from Mouse Lungs

Lungs of one hundred 7-10 week old BALB/c athymic nude mice were used to prepare the lung-derived factors as previously described (Maman et al., 2013). In short, lungs were cut into pieces, suspended in serum-free medium (RPMI-1640) in a ratio of 1 ml/l lung (100 mg tissue), manually minced, and centrifuged twice for 7 min at 1,200 rpm. The lung supernatants were then collected and filtered (0.45 µm, Whatman GmbH, Germany). Lung supernatants were lyophilized and kept in −80° c. until use. The factors collected in this manner were referred hereafter as lung-derived factors.

Dialysis of Lung-Derived Factors

Lyophilized lung-derived factors were reconstituted in serum-free medium (RPMI-1640) to a concentration of 1 mg/ml, filtered (0.45 μm) and injected into a 3500 Da cutoff dialysis cassette (3.5K MWCO Slide-A-Lyzer; Thermo Scientific). The dialysis cassette was stirred for 24 hr in a 1XDulbecco's Phosphate Buffered Saline (Sigma-Aldrich) that was changed twice. Dialyzed and non-dialyzed lung-derived factors were then supplemented with 5% BSA and incubated with neuroblastoma cells for 72 hr and cell viability was assessed as described below.

HPLC Separation of Lung-Derived Factors

Lyophilized lung-derived factors were reconstituted in Milli-Q purified water (EMD Millipore) to a concentration of 1 mg/ml, filtered (0.45 μm) and subjected to separation by Alliance reversed-phase high-performance liquid chromatograph (RP-HPLC) (Waters, Milford, Mass.) system using Waters XBridge C18 column (30×150 mm, 5μm) running a gradient of 35% to 50% acetonitrile (Fisher Scientific, Pittsburgh, Pa., USA) in water containing 0.1% trifluoroacetic acid (Halocarbon, Inc., River Edge, N.J., USA) at a flow rate of 15 ml/min. Separated fractions were collected, lyophilized and reconstituted in starvation media (RPMI 5% BSA) to a concentration of 1 mg/ml. The reconstituted fractions were then filtered (0.45 μm), incubated with neuroblastoma cells at for 72 hr and cell viability was assessed as described below.

HPLC Purification of the Inhibitory Fraction of Lung-Derived Factors

The HPLC-separated fraction found to inhibit the viability of neuroblastoma cells was lyophilized and reconstituted in Milli-Q purified water (EMD Millipore, MA, USA) to a concentration of 1 mg/ml, filtered (0.45 μm) and subjected to high-resolution purification by Alliance RP-HPLC system (Waters) using Waters)(Bridge C18 column (30×150 mm, 5μm) running a gradient of 30% to 50% acetonitrile (Fisher Scientific) in water containing 0.1% trifluoroacetic acid (Halocarbon), at a flow rate of 40 ml/min. The purified fraction was collected, lyophilized, and reconstituted in starvation media (RPMI 5% BSA) to a concentration of 1 mg/ml. The reconstituted purified inhibitory fraction was then filtered (0.45 μm), incubated with neuroblastoma cells for 72 hr and cell viability was assessed as described below.

Electrospray Ionization Mass Spectrometry

Electrospray ionization mass spectrometry (ESI-MS) analyses were carried out on a Micromass ZQ-4000 single quadruple mass spectrometer (Waters). Samples were suspended in 50% methanol-1% acetic acid buffer and infused by a syringe pump at 10 μl/min. De-convolution of data was performed using the Micromass MaxEnt software.

Tryptic Digestion of the Purified Inhibitory Factor

The direct digestion of the purified inhibitory factor was performed in Coomassie stained polyacrylamide gel. Protein spots were excised from the gel and in gel digested with trypsin according to published procedures (Rosenfeld et al., 1992). The gel pieces were dehydrated in acetonitrile (Fisher Scientific), rehydrated in 10 mM dithiothreitol (DTT) in 0.1M ammonium bicarbonate and reduced at room temperature for 30 min. The DTT solution was removed and the sample alkylated 30 μl 50 mM iodoacetamide in 0.1M ammonium bicarbonate at room temperature for 30 min. The reagent was removed and the gel pieces dehydrated in acetonitrile. The acetonitrile was removed and the gel pieces rehydrated in 0.1M ammonium bicarbonate. The pieces were dehydrated in acetonitrile, the acetonitrile removed and the pieces completely dried by vacuum centrifugation. The gel pieces were rehydrated in 20 ng/μl trypsin in 50 mM ammonium bicarbonate on ice for 10 min. Any excess enzyme solution was removed and 50 mM ammonium bicarbonate added. The sample was digested overnight at 37° c. in 50% acetonitrile and 5% formic acid and evaporated to for MS analysis.

Liquid Chromatography Tandem Mass Spectrometry (LC-MS/MS)

The LC-MS system consisted of a Thermo Electron Orbitrap Velos ETD mass spectrometer system with a Protana nanospray ion source interfaced to a self-packed 8 cm×75 μm id Phenomenex Jupiter 10 μm C18 reversed-phase capillary column. The digested inhibitory factor was injected and the peptides eluted from the column by an acetonitrile-0.1M acetic acid gradient at a flow rate of 0.5 μl/min over 30 min. The nanospray ion source was operated at 2.5 kV. The digest was analyzed using the double play capability of the instrument acquiring full scan mass spectra to determine the peptide molecular mass followed by product ion spectra to determine amino acid sequence in sequential scans. The data were analyzed by database searching using the Sequest search algorithm against the Mouse International Protein Index (IPI).

Blocking the Inhibitory Effect of Lung-Derived Factors

Lung-derived factors were supplemented with 1, 10 or 100 μg/ml of either control goat IgG Isotype antibody (AB-108-C; R&D Systems) or of specific goat anti-mouse HBB2 antibody (M-19; Santa Cruz Biotechnology). The antibody-supplemented lung-derived factors were then incubated with neuroblastoma cells for 72 hr and cell viability was assessed as described below.

Orthotopic Inoculation of Tumor Cells

An orthotopic inoculation to the adrenal gland of athymic nude mice was performed with either 50 μl of PBSX1 supplemented with 5% BSA, or with $1 \times 10^6$ MicroNB cells (generated as described previously (Edry Botzer et al., 2011)) suspended in 50 μl of PBSX1 supplemented with 5% BSA. The intra-adrenal inoculation was performed as detailed here (Nevo et al., 2008). In short, anesthesia was induced by ketamine (100 mg/kg body weight) and 2% xylazine (10 mg/kg body weight) administered intraperitoneally. Tumor cells ($1 \times 10^6$/50 μl) or PBSX1 5% BSA (50 μl) were injected orthotopically into the left adrenal gland of nude mice.

Monitoring Tumor Growth and Metastasis

The development of local tumors in the adrenal gland was monitored and measured weekly with an external digital caliper. The tumor volume in $mm^3$ was calculated by the ellipsoid volume calculation formula: Volume=0.5×(length× width) (Tomayko and Reynolds, 1989). At the end of the experiments, local adrenal tumors were weighed.

For examining the presence of micrometastatic cells in the lungs and bone marrow of mice, organs were harvested at the end of the experiment, and immediately snap frozen in dry ice. RNA was isolated from frozen tissues and used for the generation of first-strand cDNA using an M-MLV Reverse Transcriptase (See below, "RNA preparation and Reverse Transcription Polymerase Chain Reaction"). Quantification of human cells in mouse organs was determined by quantitative real-time PCR (qRT-PCR) assays.

RNA Preparation and Reverse Transcription Polymerase Chain Reaction

Total cellular RNA was extracted using EZ-RNA Total RNA Isolation Kit (Biological Industries) according to the manufacturer instructions. RNA concentrations were determined by the absorbance at 260 nm and quality control standards were A260/A280=1.8-2.0. RNA samples were used for cDNA synthesis using the M-MLV Reverse Transcriptase (Applied Biosystems Inc.) according to the manufacturer's instructions.

Quantitative Real-Time PCR

Quantification of cDNA was performed on Rotor-gene 6000™ (Corbett life science, Australia), utilizing Rotor gene 6000 series software. Reactions were run in triplicates. Transcripts were detected using SYBR Green I (Thermo Fisher Scientific, ABgene, Hamburg, Germany), according to the manufacturer instructions. The reaction primers designed based on gene sequences obtained from the GenBank Nucleotide Database of the NCBI website are described in Table 1. The mRNA concentration of the target genes was normalized to the mRNA concentration of the normalizing housekeeping genes, human beta-2-microglobulin (hβ2M) or mouse beta-2-microglobin (mβ2M). The detection of micrometastatic human neuroblastoma cells in mouse tissues was performed as previously described (Edry Botzer et al., 2011).

TABLE 1

| Gene Name | Specificity | Accession Number | Sequence | SEQ ID NO: |
|---|---|---|---|---|
| β2M | Human | NM_004048.2 | S- 5'-ATGTAAGCAGCATCATGGAG-3' | 7 |
|  |  |  | AS- 5-'AAGCAAGCAGAATTTGGAAT-3' | 8 |
| β2M | Mouse | NM_009735.3 | S- 5'-CTGGTCTTTCTGGTGCTTGT-3' | 9 |
|  |  |  | AS- 5'-GGCGTGAGTATACTTGAATTTGAG-3' | 10 |
| CXCL10 | Mouse | NM_021274.2 | S- 5'-CTATCCTGVVVACGTGTGA-3' | 11 |
|  |  |  | AS- 5'-CTTGATGGTCTTAGATTCCGG-3' | 12 |
| CX3CL1 | Mouse | NM_009142.3 | S- 5'-GGCCGCGTTCTTCCATTTGT-3' | 13 |
|  |  |  | AS- 5'-GATTTCGCATTTCGTCATGC-3' | 14 |
| HBB2 | Mouse | NM_016956.3 | S- 5'-GTGACAAGCTGCATGTGGAT-3' | 15 |
|  |  |  | AS- 5'-AGGTGGTGGCCCAGCACAAT-3' | 16 |

S-sense primer, AS-antisense primer.

Fixation and Sectioning of Frozen Tissues

Lungs of athymic nude mice that were orthotopically inoculated to the adrenal gland with either PBSX1 (normal mice) or MicroNB cells (micrometastasis-bearing mice) were washed in cold PBSX1 and put in 4% paraformaldehyde (Bio-Lab Ltd., Jerusalem, Israel) for 2 hr. Lungs were then put in 0.5M sucrose for 1 hr and in 1M sucrose in 4° C. over night. Lungs were embedded in OCT (Tissue-Tek; Bar-Naor Ltd, Israel) for 1 hr in 4° C. and then frozen in OCT on dry ice. Blocks were stored in −80° C. until sectioning. Sections of 10 μM were cut by Leica CM1860 Clinical histphatology cryostat (Leica Biosystems, Nussloch GmbH, Germany), mounted on Superfrost slides (Menzel-Glazer, Braunschweig, Germany) and air dried for 20 min. Slides were stored in −80° c. until immunofluorescence staining.

Immunofluorescence of Frozen Tissue Sections

Paraformaldehyde-fixed, OCT-embedded 10 μm thick sections of mouse lungs were washed 3 times in PBSX1 and blocked with serum-free protein block (X0909; DakoCytomation) for 10 min. Sections were incubated with HBB2 diluted 1:50 in PBSX1 (See "Antibodies") for 1 hour at room temperature followed by 3 times wash with PBSX1. Appropriate fluorescently conjugated secondary antibodies were then incubated with the slides for 30 minutes at room temperature. Coverslips were mounted on fluorescently labeled tissue using Vectamount mounting medium with DAPI (Vector Laboratories Burlingame, Calif., USA). Fluorescent images were collected with a 63×1.4 oil objective in a Leica DM4000B fluorescence microscope using Leica LAS AF software (Leica Biosystems). Tissues were stained with secondary antibodies as controls.

Protein Extraction from Mouse Organs

Lungs, bone marrow and liver of normal mice or of micrometastasis-bearing mice were washed twice in ice-cold PBSX1 and 100 mg tissue was minced manually in 500 μl ice-cold organ lysis buffer (0.05% Tween-20, 0.01% Sodium azide, 2 μg/ml aprotinin, 2 μg/ml leupeptin and 1 mM PMSF in DDW). Lysates were incubated for 20 min on ice. Supernatants were collected after centrifugation at 16,000 g for 20 min at 4° C. BCA Protein Assay (Pierce, Thermo Scientific) was used to determine protein concentration. Clarified extracts were aliquoted and stored at −80° C. until used in western blot and Enzyme-Linked Immunosorbent Assays (ELISA).

Protein Extraction from Neuroblastoma Cells

Neuroblastoma cells were washed twice with ice-cold PBSX1 and lysed with RIPA lysis buffer as previously described (Edry Botzer et al., 2011). Lysates were incubated for 20 min on ice and cleared by centrifuging at 16,000 g for 20 min at 4° C. BCA Protein Assay (Pierce, Thermo Scientific) was used to determine protein concentration. Clarified extracts were aliquoted and stored at −80° c. until used in western blot analyses.

Western Blotting

Lysates of neuroblastoma cells and of mouse organs were resolved on SDS-PAGE after the addition of Laemmli sample buffer, and transferred onto nitrocellulose membrane. The total amount of protein in the lanes was assessed by Ponceau staining prior to blocking of the membrane. The membrane was blocked at room temperature with 3% BSA (Sigma-Aldrich) diluted in TBS-Tween (TBST) for 1 hr. For detection of the target proteins, membranes were incubated with relevant primary antibodies (see "Antibodies"), then washed 3 times×5 min with TBSTX1 and incubated with suitable HRP-conjugated secondary antibodies (see "Antibodies"). Membranes were washed again 5 times×3 min with TBSTX1. The bands were visualized by chemiluminescence-ECL reactions and autoradiography by exposure to Fuji film. The amount of the relevant protein in the lanes was estimated by densitometry using Scion Image software (Scion, Frederick, Md., USA).

Collection of Mouse Serum

Blood was collected from normal and micrometastasis-bearing mice from the retro-orbital plexus. One eyeball was pulled out and blood was collected into 1.5 ml tube. Tubes were stored at room temperature for 1 hr. Tubes were then centrifuged for 15 min in 1500 g at 4° C. and serum supernatants were collected and stored in −80° C. until used in western blot and ELISA assays.

Enzyme-Linked Immunosorbent Assay

To determine the expression of mouse HBB2 in the serum of normal mice and of micrometastasis-bearing mice, HBB2 levels in mouse serum (see "Collection of mouse serum") were determined by Enzyme-Linked Immunosorbent Assays (ELISA), using standard curves of mouse recombinant HBB2 (ChinaPeptides Co, Ltd, Shanghai, People's Republic of China) at the linear range of absorbance. The following antibodies were used: Coating: 5 μg/ml goat anti-mouse Hemoglobin β antibody (M-19; Santa Cruz), detection: 0.25m/ml biotinylated rabbit anti-mouse Hemoglobin β antibody (Cusabio, Wuhan, People's Republic of China). Following the addition of Avidin-HRP (PeproTech, Inc., Rocky Hill, N.J.), the substrate ABTS (PeproTech, Inc.) was added, and color development was monitored with a Bio-Tek FL500 ELISA plate reader (Bio-Tek Instruments, Winooski, Vt., USA) at 405 nm with wavelength correction set at 650 nm, according to the manufacturer instructions. The results obtained in ELISA assays were verified in western blot analyses.

HPLC Separation of Native Human Hemoglobin

Native human hemoglobin was dissolved in Milli-Q purified water (EMD Millipore) to a concentration of 1 mg/ml and filtered (0.45 μm). Human hemoglobin was then chromatographed by Alliance RP-HPLC system (Waters) using Waters)(Bridge C18 column (50×250 mm, 10 μm) running a gradient of 35% to 50% acetonitrile (Fisher Scientific) in water containing 0.1% trifluoroacetic acid (Halocarbon) at a flow rate of 40 ml/min. The alpha and beta subunits of hemoglobin (HBA and HBB, respectively) separated in the chromatography were collected and purified by reversed phase HPLC and their molecular masses were verified by ESI-MS (see "Electrospray ionization mass spectrometry"). The purified HBA and HBB subunits were lyophilized and kept in −80° C. until use.

Cell Cycle Analysis

Neuroblastoma cells ($5 \times 10^5$) were plated and after 24 hr, cells were incubated for 48 hr with HBB diluted in starvation medium (RPMI 5% BSA) to a concentration of 10 μg/ml. Neuroblastoma cells incubated with starvation medium containing BSA alone served as control. Cells were pelleted, washed and resuspended in 0.5 ml PBSX1, containing 0.05 ml propidium iodide (PI) (P-4170, Sigma) (50 μg/ml), and 0.05 ml Triton X-100 (Sigma-Aldrich). Flow cytometry analysis was performed using Becton Dickinson FACSort and CellQuest software (Becton Dickinson, Mountain View, Calif.).

Cyclin D1 Expression

Neuroblastoma cells ($5 \times 10^6$) were plated and after 24 hr cells were incubated for 48 hr with human HBB diluted in starvation medium (RPMI 5% BSA) to a concentration of 10 μg/ml. Neuroblastoma cells incubated with starvation medium containing BSA alone served as control. At the end of the incubation period, cells were lysed (see "Protein extraction from neuroblastoma cells"), resolved on SDS-PAGE, and transferred onto nitrocellulose membrane (see "Western blotting"). Cyclin D1 expression was calculated in reference to β-tubulin expression in the lane as measured by densitometry using Scion Image software (Scion).

ERK1/2, p38 and TAK1 Phosphorylation

Neuroblastoma cells ($5 \times 10^6$) were plated and after 24 hr the growth medium was replaced with starvation medium (RPMI 0.5% FCS) for 24 hr. Cells were then washed and incubated for 30 min with human HBB, diluted in starvation medium (RPMI without BSA) to a concentration of 10 μg/ml. Neuroblastoma cells incubated with starvation medium alone served as control. At the end of the incubation period, cells were lysed (see "Protein extraction from neuroblastoma cells"), resolved on SDS-PAGE, and transferred onto nitrocellulose membrane (see "Western blotting"). ERK1/2 phosphorylation was calculated in reference to total ERK2 protein, p38 and TAK1 phosphorylation was calculated in reference to total p38 and TAK1, respectively, as measured by densitometry using Scion Image software (Scion).

Inhibition of p38 MAP Kinase

Neuroblastoma cells were seeded ($3 \times 10^4$ per well) in a 96-well flat-bottomed tissue culture plate. After an incubation of 24 hr, cells were washed and incubated with human HBB diluted in starvation medium (RPMI 5% BSA) to a concentration of 10 μg/ml. The p38 MAP kinase inhibitors SB203580 (559389; Calbiochem, EMD Millipore) and SB202190 (152121-30-7; Calbiochem, EMD Millipore) were added in a concentration of 0.1, 1 and 10 μM to the neuroblastoma cells incubated with HBB. Cells incubated with HBB only or p38 MAP kinase inhibitors only served as control. After 72 hr of incubation cell viability was assessed as described below.

Cleavage of Human HBB into Two Fragments

Human HBB was incubated at a concentration of 2 mg/ml with 50 mg/ml CNBr (Sigma-Aldrich) in 5% trifluoroacetic acid (Halocarbon). After an overnight cleavage at room temperature, the resulting fragments of human HBB were purified by Alliance RP-HPLC system (Waters) using Waters)(Bridge C18 column (30×150 mm, 5 μm) running a gradient of 35% to 50% acetonitrile (Fisher Scientific) in water containing 0.1% trifluoroacetic acid (Halocarbon), at a flow rate of 15 ml/min. Two products resulted, N-terminal and C-terminal fragments of human HBB, and their molecular masses were verified by ESI-MS (see "Electrospray ionization mass spectrometry"). The N- and C-terminal fragments of human HBB were incubated with neuroblastoma cells. After 72 hr of incubation cell viability was assessed as described below.

Solid-Phase Synthesis of Human HBB Segments

FMOC solid-phase synthesis was used to synthesize human HBB in 14 peptide segments of 15 amino acid residues each. Each segment was composed of 5 amino acid residues overlapping those of the preceding segment and 5 amino acid residues overlapping those of the following segment. Peptide sequences appear in Table 2. Peptide segments of human HBB were purified to homogeneity by RP-HPLC, and their molecular masses were ascertained by ESI-MS by ChinaPeptides (ChinaPeptides.Co, Ltd). HBB peptide segments were lyophilized and reconstituted in starvation media (RPMI 5% BSA) to a concentration of 1, 10 or 100 μg/ml. The reconstituted peptides were then filtered (0.45 μm), incubated with neuroblastoma cells at for 72 hr and cell viability was assessed as described below.

TABLE 2

Artificial Sequence

| Human HBB Peptide Segment | Peptide Sequence | SEQ ID NO: |
|---|---|---|
| 1 | VHLTPEEKSAVTALW | 17 |
| 2 | VTALWGKVNVDEVGG | 18 |
| 3 | DEVGGEALGRLLVVY | 19 |

TABLE 2-continued

Artificial Sequence

| Human HBB Peptide Segment | Peptide Sequence | SEQ ID NO: |
|---|---|---|
| 4 | LLVVYPWTQRFFESF | 20 |
| 5 | FFESFGDLSTPDAVM | 21 |
| 6 | PDAVMGNPKVKAHGK | 22 |
| 7 | KAHGKKVLGAFSDGL | 23 |
| 8 | FSDGLAHLDNLKGTF | 24 |
| 9 | LKGTFATLSELHCDK | 25 |
| 10 | LHCDKLHVDPENFRL | 26 |
| 11 | ENFRLLGNVLVCVLA | 5 |
| 12 | VCVLAHHFGKEFTPP | 27 |
| 13 | EFTPPVQAAYQKVVA | 28 |
| 14 | QKVVAGVANALAHKYH | 29 |

Solid-Phase Synthesis of Metox and Scrambled-Metox Peptides

The short inhibitory C-terminal human HBB peptide (ENFRLLGNVLVCVLA; SEQ ID NO:5) designated "HBB11p" or "Metox", and a control peptide of a scrambled amino acid sequence (ANVLNECVFVGRLLL; SEQ ID NO:6) designated scrambled-Metox, were chemically synthesized. The synthesis was performed on appropriate PAM resins (Applied Biosystems) on an 433A peptide synthesizer (Applied Biosystems) using an optimized HBTU (Oakwood Chemical, West Columbia, S.C., USA) activation/DIEA (Sigma-Aldrich) in-situ neutralization protocol developed by Kent and coworkers for Boc solid-phase peptide synthesis (Schnolzer et al., 1992). After chain assembly, the peptides were cleaved by anhydrous hydrogen fluoride (Airgas, PA, USA) in the presence of 5% p-cresol (Sigma-Aldrich) at 0° C. for 1 hr, followed by precipitation with cold ether. The Metox and scrambled-Metox peptides were purified to homogeneity by reversed-phase HPLC, and their molecular masses were ascertained by ESI-MS (see "Electrospray ionization mass spectrometry").

Conjugation of Metox Peptide to FITC

After chain assembly during Metox synthesis (see "Solid-phase synthesis of Metox and scrambled-Metox peptides"), Metox resin was conjugated to FITC (Life Technologies). The conjugation reaction proceeded overnight in DMF as solvent, in the molar Metox/FITC/DIEA ratio of 1:1.2 4. After hydrogen fluoride (Airgas, PA, USA) cleavage, crude Metox-FITC was dissolved in 50% Acetonitrile Confocal Microscopy for Metox Cell Entry Neuroblastoma cells seeded on glass coverslips ($8\times10^4$ per coverslip) overnight were treated with FITC-conjugated Metox at a concentration of 10 μg/ml. The cells were washed with PBS after 30, 60 and 120 min of incubation with FITC-Metox and then fixed using 4% formaldehyde for 30 min. Coverslips were mounted on glass slides using Vectamount mounting medium with DAPI (Vector Laboratories Burlingame, Calif., USA). Cells were analyzed by Leica TCS SP5 confocal microscope.

Treating Mice with Metox

Mice were orthotopically inoculated with MicroNB cells to the adrenal gland to generate local adrenal tumors and lung and bone marrow micrometastasis (see "Orthotopic inoculation of tumor cells"). Fourteen days post tumor cell inoculation mice were treated either intravenously or intranasally with 1 mg/kg (0.02 mg/mouse) of the short inhibitory human HBB peptide, Metox, once a week for 8 weeks.

For intranasal administration of Metox, the lyophilized peptide was dissolved prior to each administration in Dimethyl Sulfoxide (DMSO) (Sigma-Aldrich) to a concentration of 0.013 mg/μl, and then diluted in sterile PBSX1 to a concentration of 0.4 μg/μl. The dissolved peptide was filtered (0.2 μm) and mice were forced to inhale 50 μl of Metox (0.02 mg/mouse). Control group was forced to inhale 50 μl of a control scrambled peptide, scrambled-Metox (see "Solid-phase synthesis of Metox and scrambled-Metox peptides").

Statistical Analysis

Paired or unpaired Student t test was used to compare in-vitro and in-vivo results.

Figure 1B:
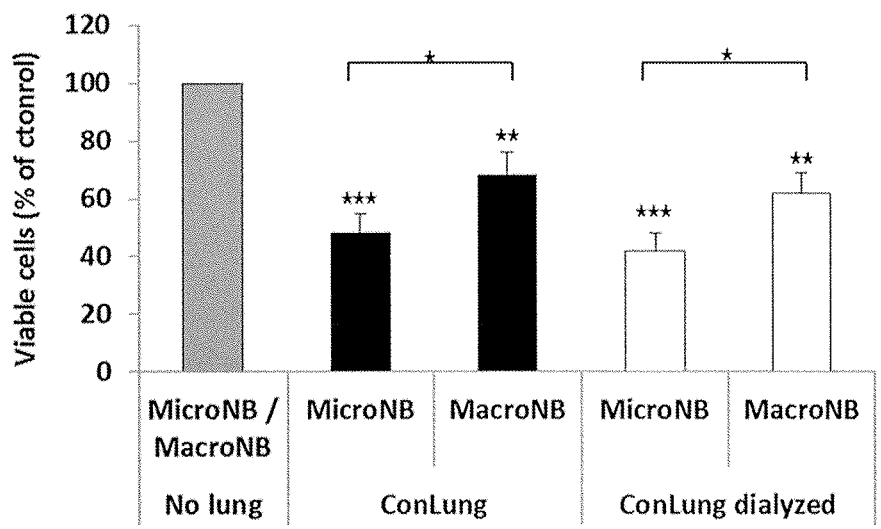

Example 1. Lung-Derived Soluble Extracts Significantly Inhibited the Viability of MicroNB Cells Mouse lungs (ConLung) were harvested, minced and filtered, and soluble factors were collected as described above and as shown in FIG. 1A. Dialyzed and non-dialyzed lung-derived factors were prepared and incubated with MicroNB and MacroNB cells that were seeded ($3\times10^4$ per well) a day earlier in a 96 well flat-bottomed tissue culture plate. After an incubation of 72 hr cell viability was assessed using an MTS-based viability assay. The MTS-based viability assays indicated that dialyzed (3500 MW Da cutoff) lung-derived factors inhibited cell viability to the same extent as non-dialyzed lung-derived factors. The results are shown in FIG. 1B. Data are means of three independent experiments±SD. Significance was evaluated using Student's t-test for the percentage of viable cells after incubation of MicroNB and MacroNB cells with dialyzed and non-dialyzed lung-derived factors compared to incubation with control media (No lung). Macro metastatic neuroblastoma cells (MacroNB) were found to be less sensitive to the lung-derived restraining factors and may have acquired resistance to these factors, thereby escaping their surveillance.

Figure 1C:
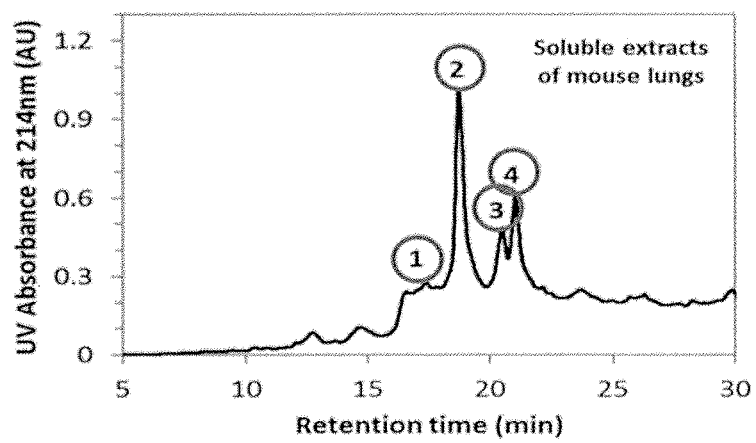
Figure 1D:
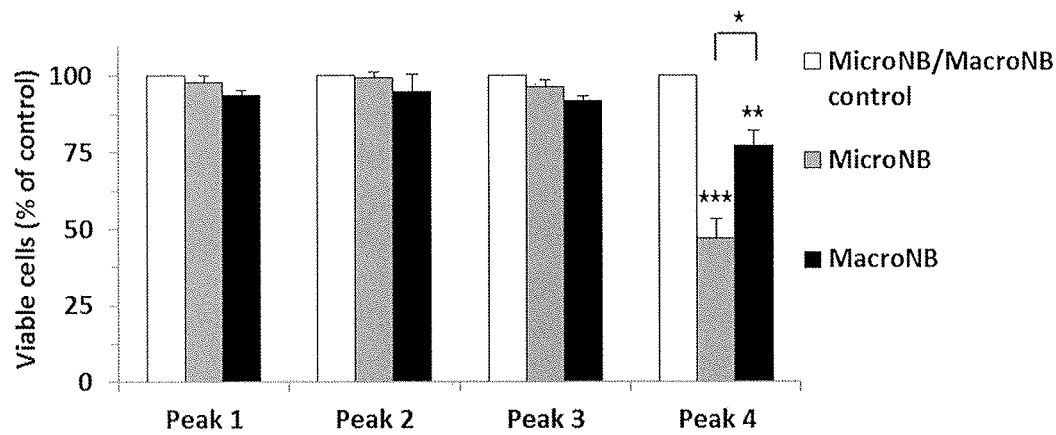
Figure 1E:
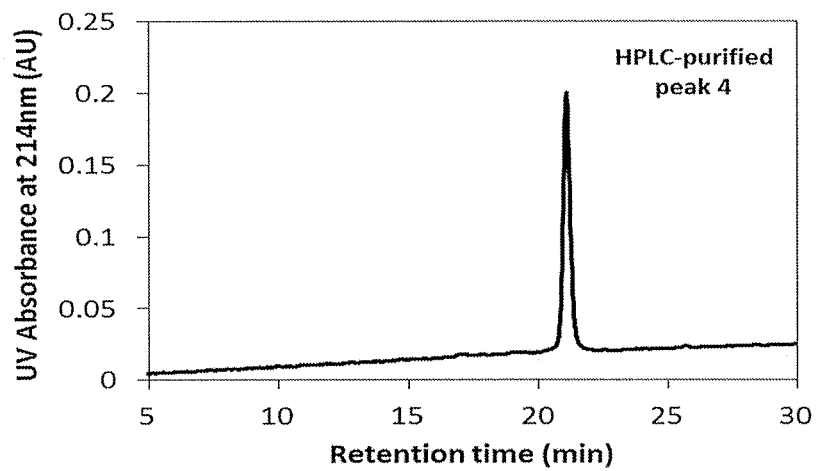

Given that the inhibitory activity of lung-derived factors was not impaired after a dialysis using a 3500 Da membrane cassette, the molecular weight of the inhibitory factor was predicted to be higher than 3500 Da. FIG. 1C shows that reversed-phase HPLC separation of dialyzed lung-derived factors resulted in four distinctive peaks. FIG. 1D shows the results from an MTS-based viability assay and trypan blue exclusion assays which revealed that peak no. 4 inhibited cell viability when incubated with micrometastatic (MicroNB) and macrometastatic (MacroNB) neuroblastoma cells for 72 hr. Data are means of three independent experiments±SD. Significance was evaluated using Student's t-test for the percentage of viable cells after incubation of MicroNB and MacroNB cells with HPLC-separated peaks of lung-derived factors compared to incubation with control media (No lung). FIG. 1E shows that HPLC purification of peak no. 4 resulted in one peak.

Example 2. Isolation and Identification of Inhibitory Lung Factor

Figure 2A:
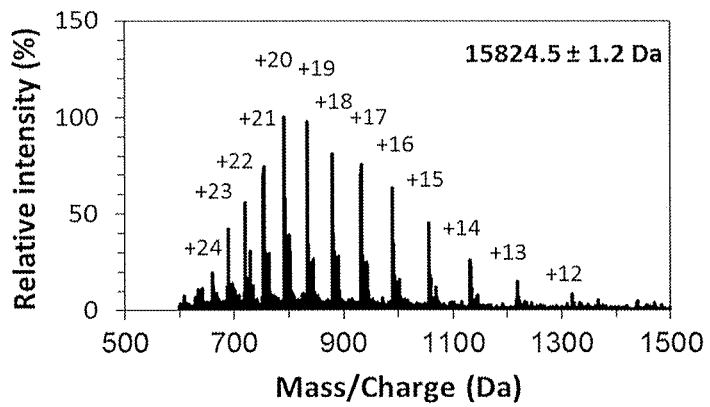
FIGS. 2A-2C. Identification of the isolated inhibitory lung factor.
Figure 2B:
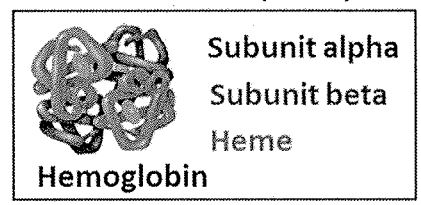

Identification of the isolated inhibitory lung factor. Electrospray ionization mass spectrometry (ESI-MS) analysis of the HPLC-separated peak no. 4 indicated that the peak harbored a single protein of a MW of 15824.5 Da (FIG. 2A). Sequence analysis by liquid chromatography-tandem mass spectrometry LC-MS/MS coupled with tryptic digestion of the inhibitory peak no. 4 revealed a 147 amino acid sequence (FIG. 2B). Database search in the International Protein Index (IPI) revealed a 100% identity to the mouse beta subunit of hemoglobin (HBB2). HBB2 has the following amino acid sequence:

(SEQ ID NO: 1; GenBank accession number: Q549D9)
MVHLTDAEKSAVSCLWAKVNPDEVGGEALGRLLVVYPWTQRYFDSFGD

LSSASAIMGNPKVKAHGKKVITAFNEGLKNLDNLKGTFASLSELHCDK

LHVDPENFRLLGNAIVIVLGHHLGKDFTPAAQAAFQKVVAGVATALAH

KYH

Figure 2C:
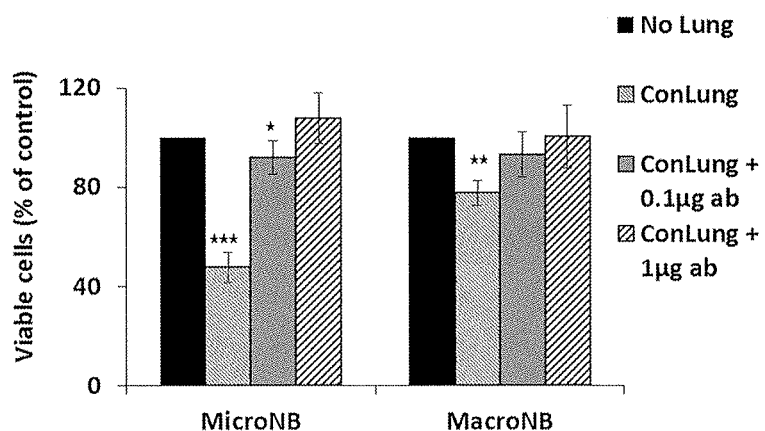

HBB2 was verified as the inhibitory lung factor when the addition of a specific anti-mouse HBB2 antibody blocked the inhibitory activity of lung-derived factors incubated with MicroNB and MacroNB cells, as indicated in an MTS-based viability assay (FIG. 2C). Lung-derived factors were supplemented with 0.1, 1 or 10 µg of either control goat anti mouse IgG Isotype antibody (Jackson Immuno Research Laboratories) or of specific goat anti mouse HBB2 antibody (M-19; Santa Cruz). The antibody supplemented lung-derived factors were then incubated with MicroNB and MacroNB cells that were seeded (3×10$^4$ per well) a day earlier in a 96 well flat-bottomed tissue culture plate. After an incubation of 72 hr, cell viability was assessed using an MTS-based viability assay (CellTiter 96® AQueous One Solution Cell Proliferation Assay, Promega) according to the manufacturer instructions. Data are means of three Independent experiments±SD. Significance was evaluated using Student's t-test for the percentage of viable cells after incubation of MicroNB and MacroNB cells with lung-derived factors (Conlung) or with lung-derived factors supplemented with a specific anti-mouse HBB2 antibody (Conlung+ab) compared to incubation with control media (No lung).

Example 3. Human Hemoglobin Beta Inhibits Viability of Neuroblastoma Cells

Figure 3A:
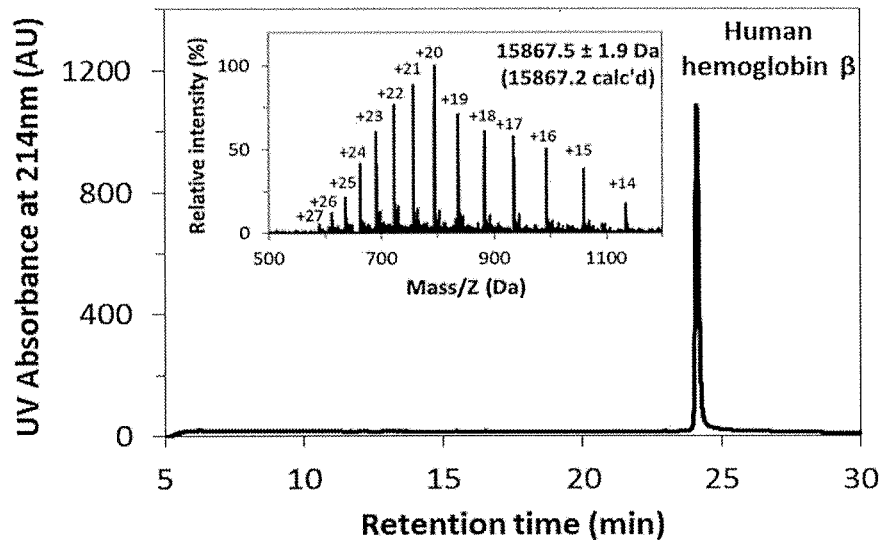
FIGS. 3A-3E. Isolation and characterization of human HBB.

The beta subunit of human hemoglobin (HBB) is known to be expressed ubiquitously in normal human lungs (Ishikawa et al., 2010). Whether HBB also has the capacity to inhibit the viability of human neuroblastoma metastases and micrometastases was investigated. Native human hemoglobin (Sigma) was dissolved in Milli-Q purified water (Millipore Corporation) and filtered (0.45 µm; Whatman GmbH, Germany). Human hemoglobin was then chromatographed by C18 reversed phase HPLC running a gradient of 30% to 50% acetonitrile in water containing 0.1% TFA at a flow rate of 1 ml/min. The alpha and beta subunits of hemoglobin separated in the chromatography were collected and purified by reversed phase HPLC and their molecular masses were verified by electrospray ionization mass spectrometry (ESI-MS). The beta subunit (HBB) had a MW of 15867 Da (FIG. 3A).

The 147 amino acid sequence of wild-type human HBB is as follows:

(SEQ ID NO: 2; GenBank accession number: P68871)
MVHLTPEEKSAVTALWGKVNVDEVGGEALGRLLVVYPWTQRFFESFGD

LSTPDAVMGNPKVKAHGKKVLGAFSDGLAHLDNLKGTFATLSELHCDK

LHVDPENFRLLGNVLVCVLAHHFGKEFTPPVQAAYQKVVAGVANALAH

KYH.

Figure 3B:
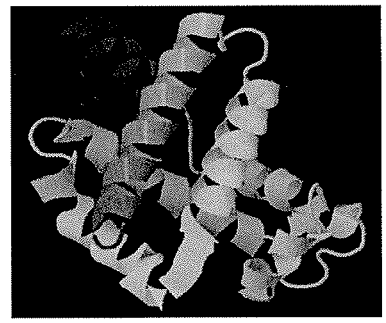
Figure 3C:
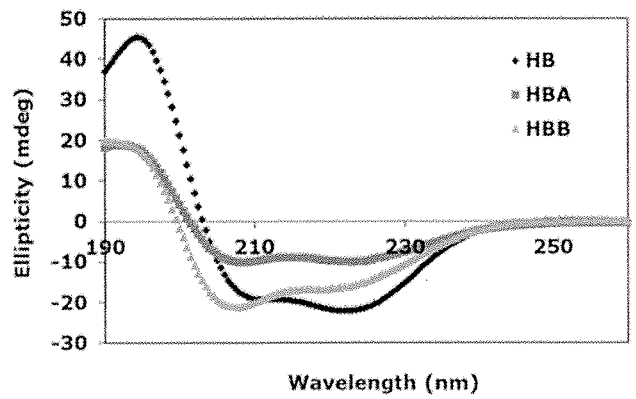
Figure 3D:
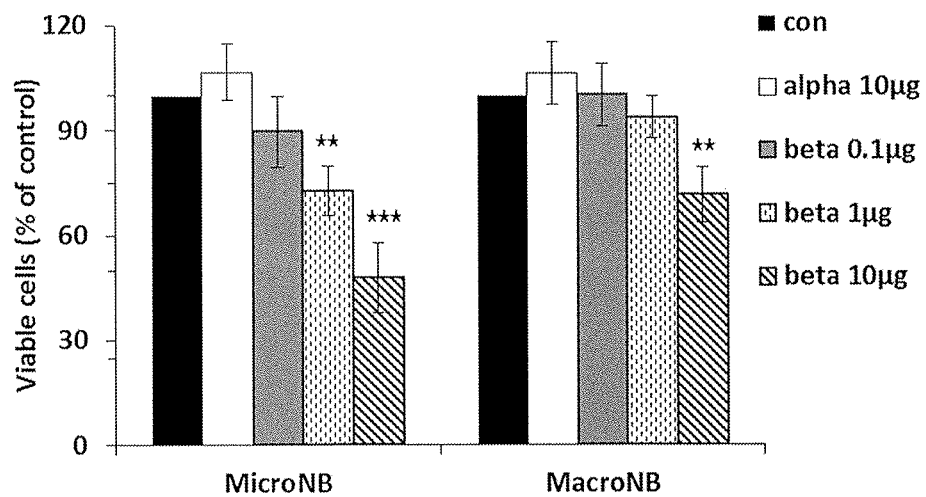

Structure prediction of human HBB by 1-TASSER tool revealed a helical structure C (FIG. 3B). Circular dichroism analysis of human hemoglobin (HB), hemoglobin subunit alpha (HBA) and subunit beta (HBB) indicated a helical structure for all three proteins (FIG. 3C). An MTS-based viability assay indicated that incubation with 10 µg human HBB decreased the viability of MicroNB cells by 52% and of MacroNB cells by 29% (FIG. 3D). HBA did not influence cell viability (FIG. 3D). Neuroblastoma cells were seeded (3×10$^4$ per well) in a 96 well flat-bottomed tissue culture plate. After 24 hr of incubation cells were washed and incubated with human HBB dissolved in starvation medium (RPMI 5% BSA) to the indicated concentrations. Cell viability under normal conditions (starvation medium) or after incubation with human HBB was monitored after an incubation of 72 hr using an MTS-based viability assay (CellTiter 96® AQueous One Solution Cell Proliferation Assay, Promega) according to the manufacturer instructions. Data are means of three independent experiments±SD. Significance was evaluated using Student's t-test for each variant incubated with human HBB compared to incubation with control media (con).

Trypan blue exclusion assays (results not shown) demonstrated that 16% and 8% of MicroNB and MacroNB cells, respectively, were non-viable following the incubation with HBB. These results were strikingly similar to the cytostatic activities mediated by mouse lung-derived factors (Maman, S. et al. (2013). *Int J Cancer* 133, 2296-2306) or by mouse lung-derived HBB2. The HBB-mediated inhibitory activity was dose dependent (results not shown).

The influence of human HBB on cell viability was assessed on numerous additional cancerous cell lines as seen in Table 3. An inhibition in cell viability was observed in two cell lines when incubated with all HBB amounts examined (1, 10 and 100 µg)—the lung carcinoma cell line A549 and the melanoma cell line RALL. When incubated with the highest amount of HBB (100 µg), the viability of the following cell lines was inhibited: the breast cancer cell lines T47D and MCF-7, the prostate cancer cell line 22RVi, the cervical cancer cell line Hela, and the melanoma cell lines RALL and RKTJ.

TABLE 3

The influence of HBB on the viability of numerous cancerous cell lines.

| Cell line | Tumor type | % difference in cell viability (1 µg HBB) | % difference in cell viability (10 µg HBB) | % difference in cell viability (100 µg HBB) |
| --- | --- | --- | --- | --- |
| MDA-231 | Breast | No change | +5% | No change |
| MDA-MB-468 | | No change | No change | No change |
| T47D | | No change | -8% | -30% |
| MCF-7 | | No change | No change | -26% |
| SKBR3 | | No change | No change | No change |
| SW480 | Colon | No change | No change | No change |
| A549 | Lung | -17% | -18% | -25% |
| 22RVi | Prostate | No change | -14% | -45% |

TABLE 3-continued

The influence of HBB on the viability of numerous cancerous cell lines.

| Cell line | Tumor type | % difference in cell viability (1 μg HBB) | % difference in cell viability (10 μg HBB) | % difference in cell viability (100 μg HBB) |
|---|---|---|---|---|
| Hela | Cervix | No change | No change | −30% |
| RKTJ | Melanoma | No change | No change | −65% |
| RALL | | −11% | −25% | −55% |
| *MHH-NB11 (MicroNB) | Neuroblastoma | −23% | −42% | −62% |

*The influence of HBB on the viability of MicroNB cells served as positive control in the viability experiments.

The influence of HBB on the viability of the normal lung-residing cell lines HPEC (Human pulmonary endothelial cells) and HLMEC (Human lung microvascular endothelial cells) and on the normal kidney cell line 293T and 293A was examined as well. HBB did not influence the viability of these normal cells (data not shown).

Figure 3E:
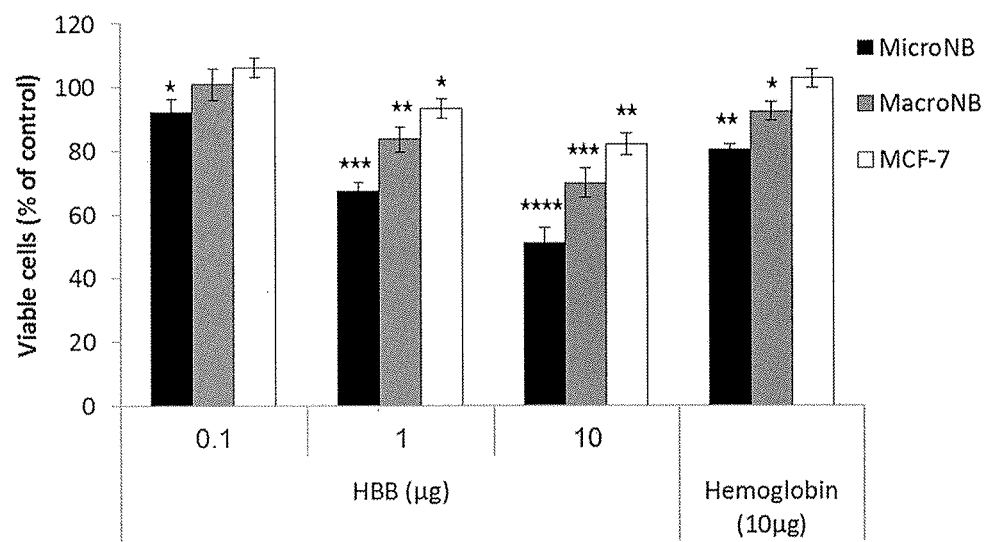

The whole human hemoglobin protein inhibited cell viability as well but not to the same extent as HBB (FIG. 3E). Data are means of three independent experiments±SD. Significance was evaluated using Student's t-test for the percentage of viable cells after incubation with human HBB compared to incubation with control media (not shown).

Example 4. Inhibition in Neuroblastoma Cell Viability Due to Cell Cycle Arrest

Figure 4A:
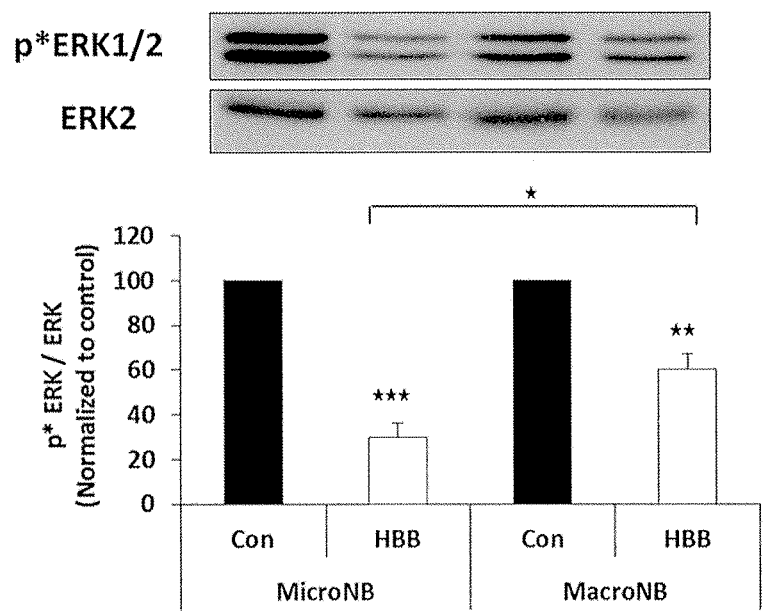
FIGS. 4A-4C. Human HBB inhibits the viability of neuroblastoma cells by a G0-G1 cell cycle arrest. Human HBB2 (1 µg) was incubated with MicroNB and MacroNB cells for 48 hr.

In order to elucidate the mechanism underlying the inhibition in cell viability caused by human HBB, MicroNB and MacroNB cells were incubated with HBB (1 μg) for 48 hr. Whole cell lysates of MicroNB and MacroNB cells were subjected to western blot analysis and immunostaining. The phosphorylation of the extracellular signal-regulated kinase (ERK), playing a central role in cell proliferation, was found to be decreased in both MicroNB and MacroNB cells (FIG. 4A) though more evidently in MicroNB cells.

Figure 4B:
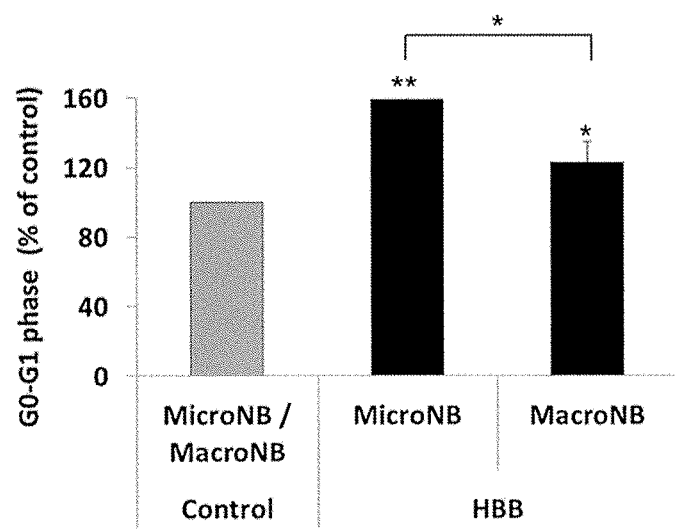

The cells were also subjected to measurement of cellular DNA content and cell cycle analysis using flow cytometry. Incubation with human HBB elevated the amount of MicroNB and MacroNB cells in the sub G0 phase, by 18% and 11%, respectively (data not shown). A notable elevation in the amount of cells in G0-G1 phase was observed in MicroNB and MacroNB cells incubated with human HBB (59% and 23% elevation, respectively) (FIG. 4B).

Figure 4C:
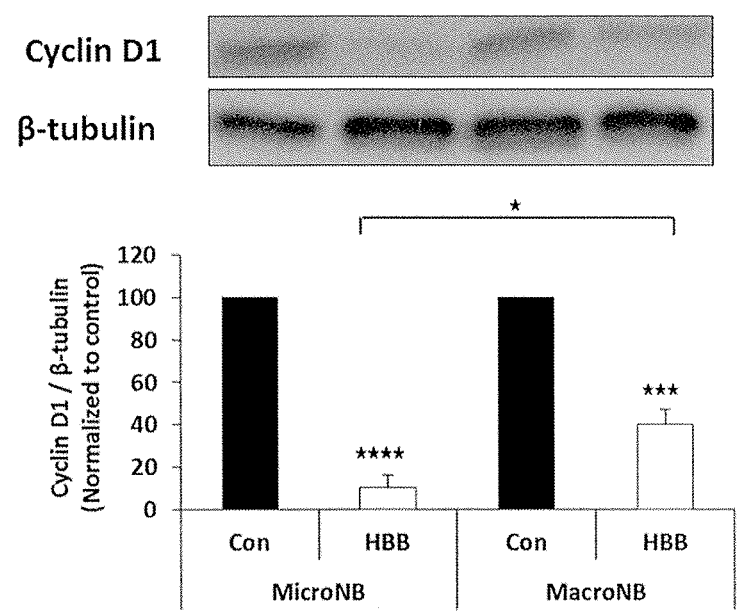

Whole cell lysates of MicroNB and MacroNB cells incubated with human HBB were subjected to western blot analysis and immunostaining. A significant decline in Cyclin-D1 expression was observed in MicroNB and MacroNB cells incubated with human HBB (FIG. 4C), supporting the evidence that HBB induces cell cycle arrest in these cells. The decrease in Cyclin-D1 expression was greater in MicroNB cells incubated with human HBB than in MacroNB cells incubated with the factor. Cyclin D1 expression was calculated in reference to beta-tubulin. Data are means of three independent experiments±SD. Significance was evaluated using Student's t-test for each analysis after incubation with HBB compared to incubation with control media.

Taken together, these results indicate that the inhibition in neuroblastoma cell viability caused by human HBB is mostly due to cell cycle arrest in G0-G1 phase. This cell cycle arrest may lead to dormancy of neuroblastoma cells, especially of MicroNB cells, that do not express a full metastatic phenotype.

Figures 5A, 5B:
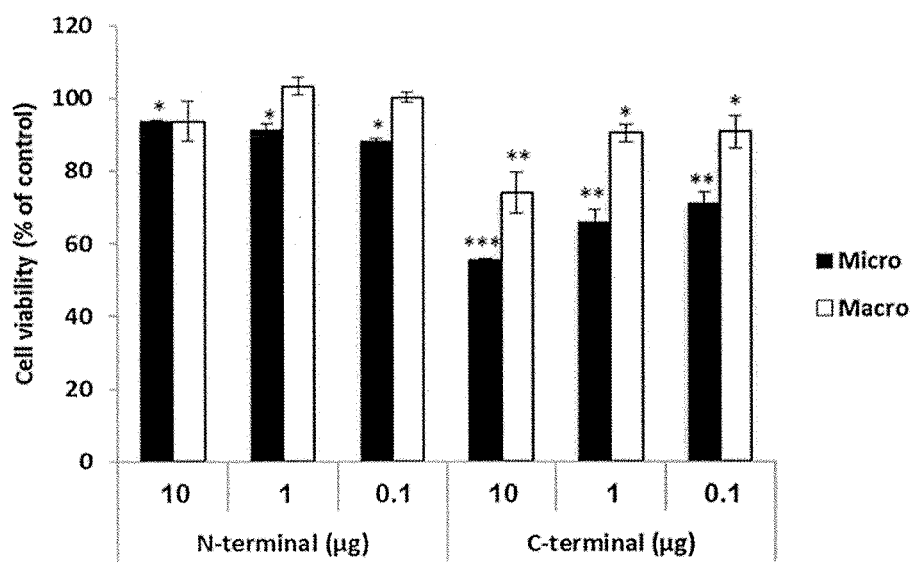
FIGS. 5A-5C. Pin-pointing the active inhibitory fragment of human HBB.

Example 5. Inhibitory Activity of HBB Lies in a Short C-Terminal Fragment of the Protein In order to pin-point the active fragment of the human HBB protein, the protein was cleaved to two fragments using cyanogen bromide (CNBr). The cleavage resulted in N- and C-terminal fragments of HBB (FIG. 5A) (SEQ ID NOs:3 and 4). The influence of these two purified fragments on neuroblastoma cell viability was examined using MTS-based proliferation assay and trypan blue exclusion assay. The results indicated that the C-terminal fragment is responsible for the inhibitory activity (FIG. 5B). The N-terminal fragment also exhibited an inhibitory effect however to a lesser extent (FIG. 5B). Data are means of three independent experiments±SD. Significance was evaluated using Student's t-test for each variant incubated with N- or C-terminal fragments of human HBB compared to incubation with control media (not shown).

Figure 5C:
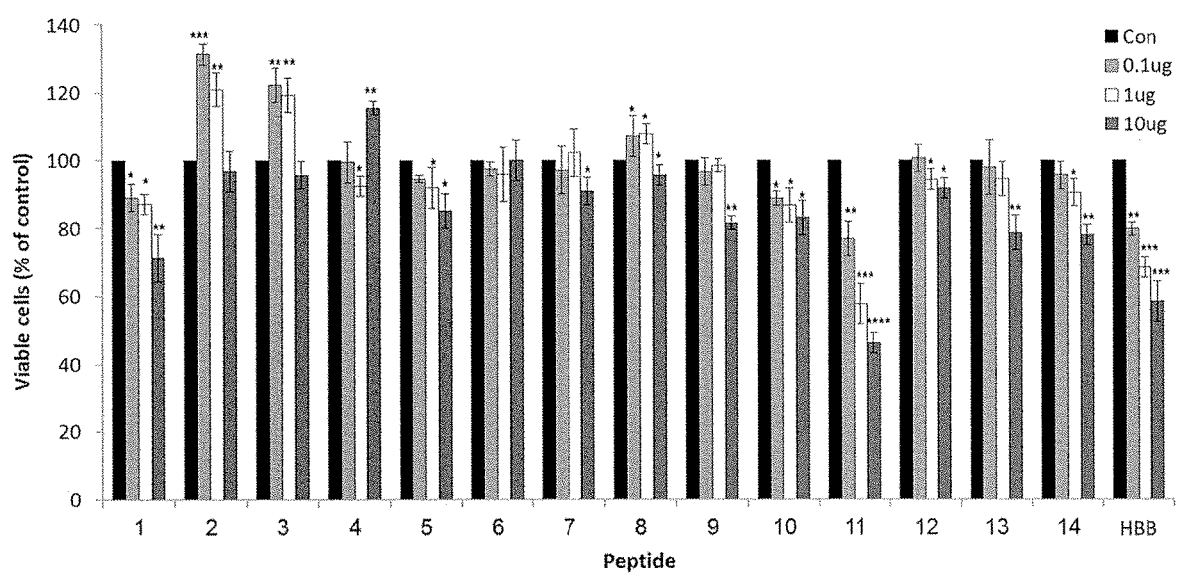

In order to narrow down the fragment responsible for the inhibitory activity of the HBB protein in a more precise manner, portions of HBB were synthesized in 14 segments, each segment comprising 15 amino acids of the protein, overlapping in 5 amino acids with the following and preceding segment. The 14 HBB peptides were incubated with MicroNB cells and examined for their influence on cell viability. Peptide number 11 (amino acid sequence ENFRLLGNVLVCVLA; SEQ ID NO:5) significantly inhibited the viability of the cells (FIG. 5C). The inhibition in cell viability caused by peptide 11 (designated HBB11p) was even greater than that caused by HBB (FIG. 5C). Data are means of three independent experiments±SD. Significance was evaluated using Student's t-test for the percentage of viable cells after incubation with each human HBB peptide compared to the percentage of viable cells after incubation with control media. Thus, a short C-terminal region of HBB is responsible for in vitro and in vivo inhibitory activity.

Example 6. HBB2 Expression is Elevated in Mice Harboring Micrometastasis

The aim of the next set of experiments was to evaluate the expression of HBB2 in lungs of normal mice and in mice bearing human neuroblastoma xenografts with clinically undetectable lung micrometastasis.

Figure 6A:
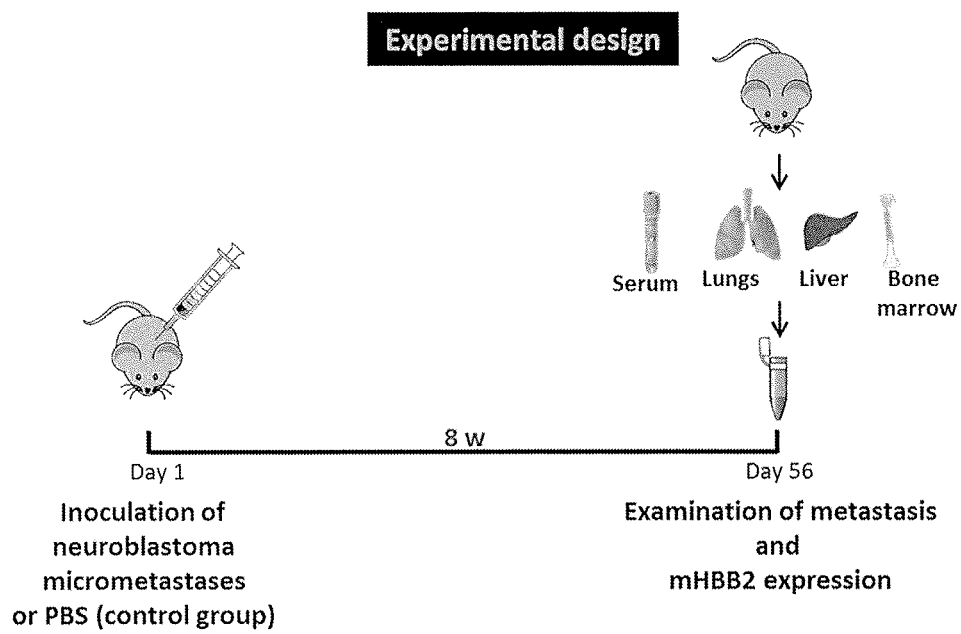
FIGS. 6A-6D. HBB2 expression is elevated in mice harboring micrometastasis. Sixteen mice were orthotopically inoculated to the adrenal gland with either neuroblastoma micrometastases or PBS (normal mice). After 8 weeks, lungs, liver and bone marrow were harvested from the mice and blood was collected (FIG. 6A). Mice organs were examined for the presence of human neuroblastoma cells using real time PCR and for mHBB2 expression using western blot analysis (FIG. 6B, FIG. 6C) and immunostaining of frozen sections (FIG. 6D).
Figure 6B:
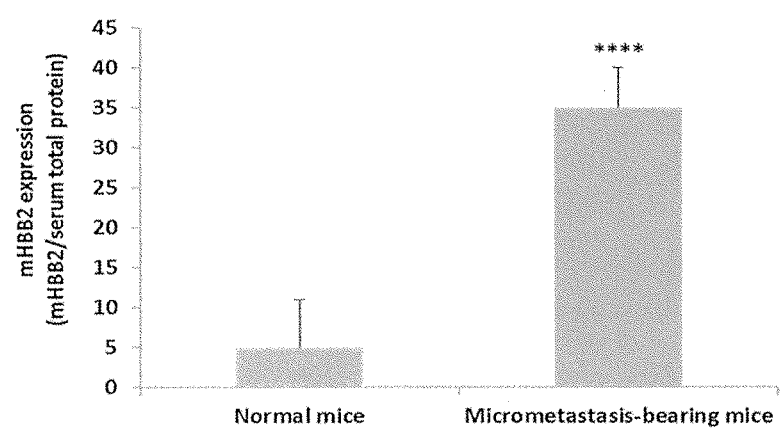
Figure 6C:
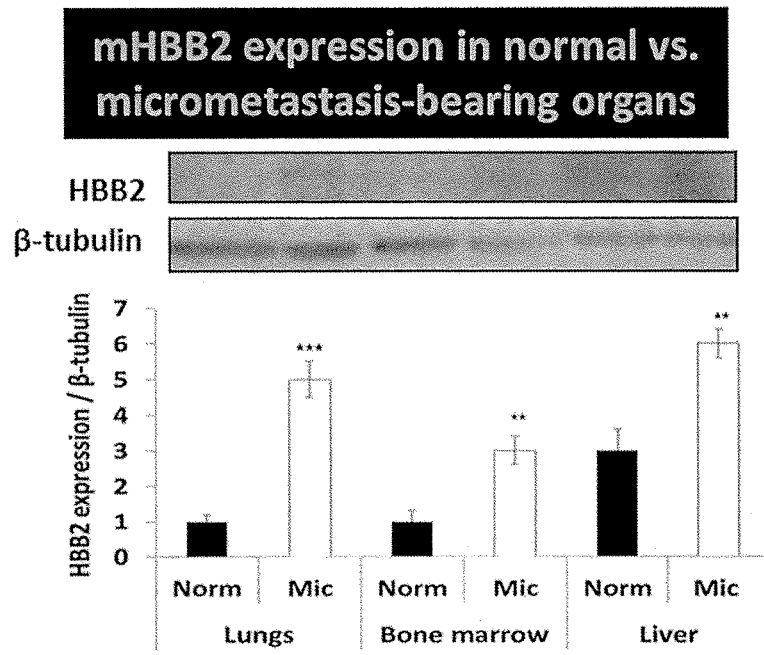
Figure 6D:
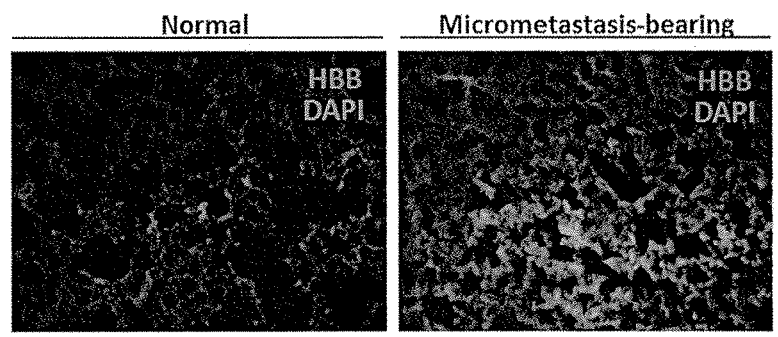

Sixteen mice were orthotopically inoculated to the adrenal gland with either neuroblastoma micrometastases or PBS (control group). After 8 weeks, lungs, liver and bone marrow were harvested from the mice and blood was collected (FIG. 6A). Mouse organs were examined for the presence of human neuroblastoma cells using real time PCR (Edry Botzer, L. et al. (2011). *Am J Path* 179, 524-536) and for HBB2 expression using western blot analysis (FIG. 6B, 6C) and immunostaining of frozen sections (FIG. 6D). HBB2 expression was significantly higher in the serum and in the organs of mice harboring micrometastasis compared to its level in the serum and organs of normal mice (FIG. 6B, 6C), implying an inducible expression of HBB2. HBB2 expression in mouse lungs was verified in frozen sections of normal (ConLung) and micrometastasis-bearing lungs (MicLung) that were fluorescently stained with anti-mouse HBB2 antibody and with DAPI. The higher expression of HBB2 in lungs harboring micrometastases was verified by western blot analysis of lung tissue lysates (FIG. 6D). Thus, HBB serves as a biomarker for the presence of clinically undetectable neuroblastoma micrometastasis and the results indicate that human neuroblastoma micrometastases induces/up-regulates the expression of HBB2 in these tissues.

Example 7. Treatment with HBB11p Inhibits Local Tumor Growth and Metastasis

Figure 7:
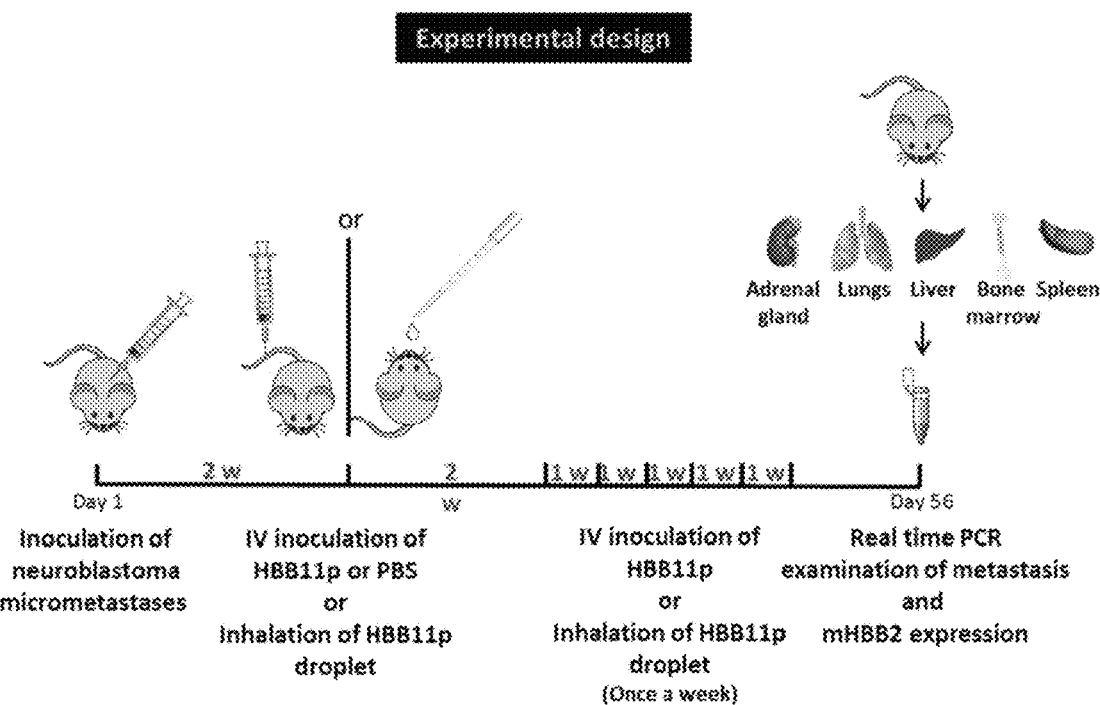
FIGS. 7A-7E. Treatment with HBB11p inhibits local tumor growth and lung metastasis. Twenty four mice were orthotopically inoculated to the adrenal gland with neuroblastoma micrometastases. Two weeks post inoculation, mice were either i.v. injected with HBB11p or forced to inhale a droplet of soluble HBB11p, once a week for 8 weeks (FIG. 7A). Mice were monitored weekly for tumor volume (FIG. 7B). At the end of the experiment, local tumors were weighed (FIG. 7C) and organs were harvested and examined for the presence of human neuroblastoma cells (FIG. 7D) and for the expression of mHBB2 (FIG. 7E) using real time PCR.
Figure 7:
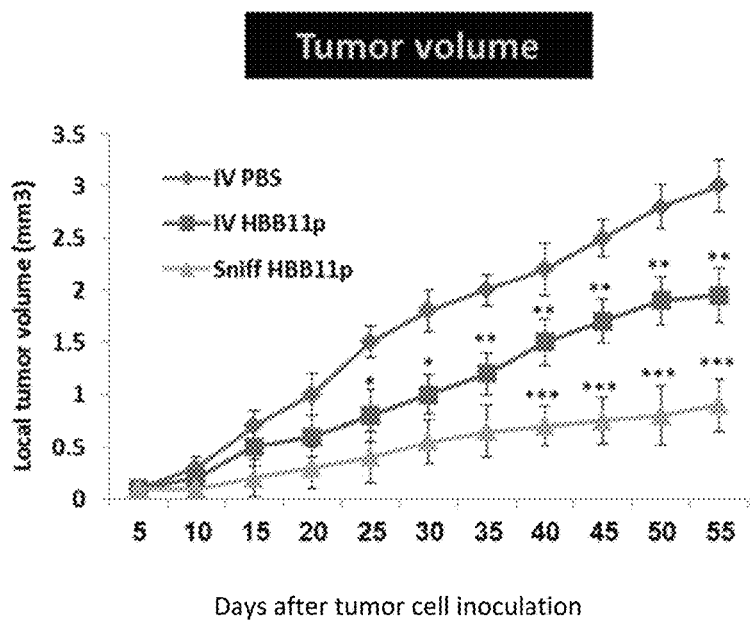

Twenty four mice were orthotopically inoculated to the adrenal gland with MicroNB cells. Two weeks post inoculation, mice were either intravenously (IV) injected with HBB11p or PBS, or forced to inhale a droplet of soluble HBB11p, once a week for 8 weeks (FIG. 7A). Mice were monitored weekly for tumor volume. At the end of the experiment, local tumors were weighed and organs were harvested and examined for human neuroblastoma cells and for HBB2 expression using real time PCR (FIG. 7A).

Figure 7C:
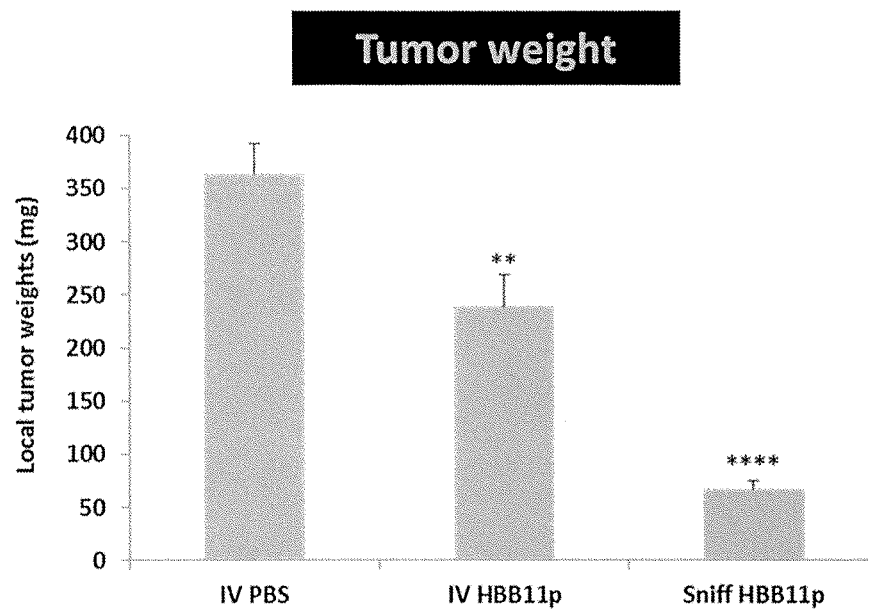
Figure 7D:
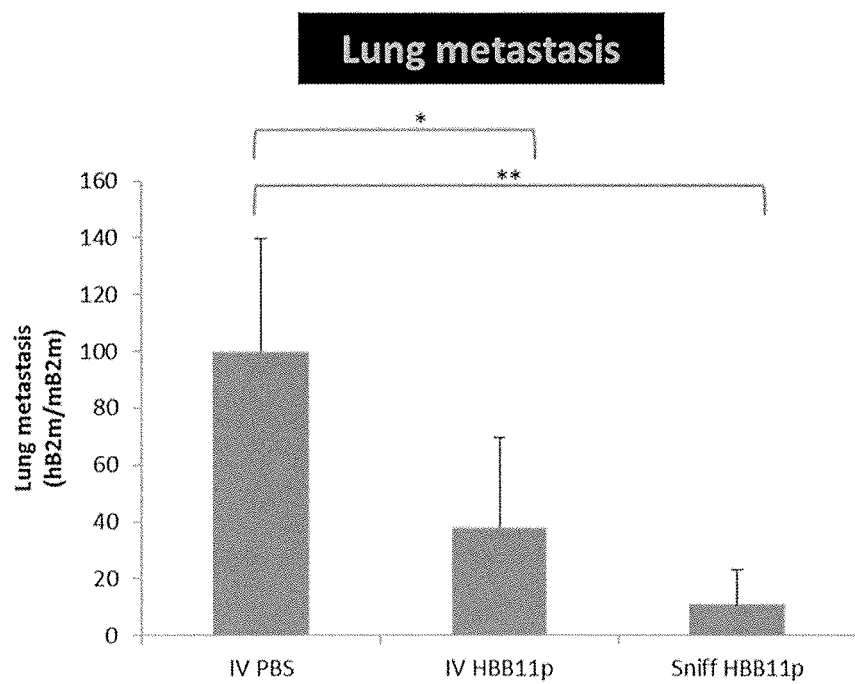
Figure 7E:
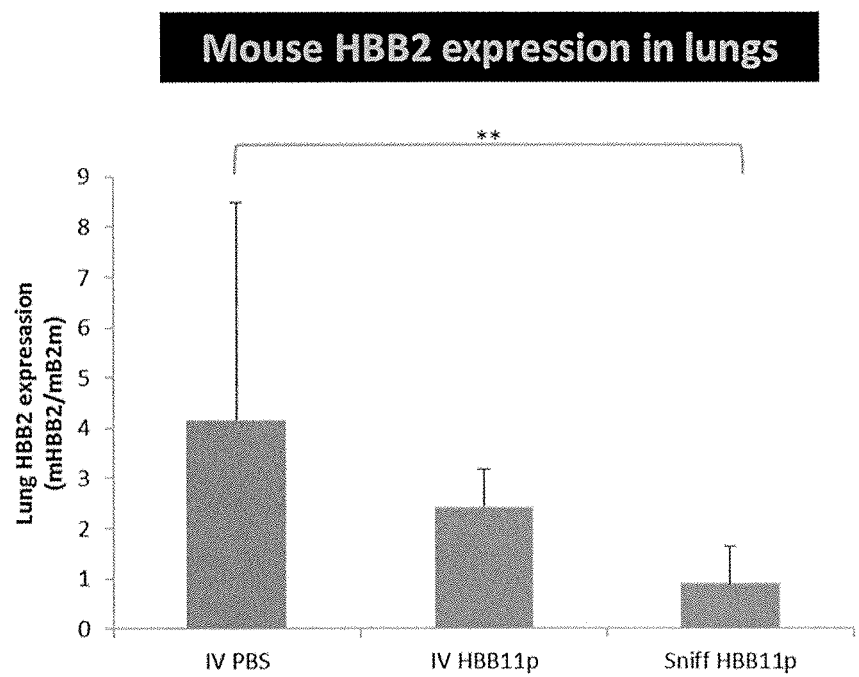

Local tumors of mice that were intravenously inoculated with HBB11p or forced to inhale a droplet of HBB11p were significantly smaller than local tumors of mice that were intravenously inoculated with PBS (FIG. 7B, 7C). Lung metastasis was significantly inhibited in mice treated with HBB11p compared to mice treated with PBS (FIG. 7D). Liver, spleen and bone marrow metastasis were significantly inhibited as well in these mice (data not shown). Using real time PCR, HBB2 expression in each organ was found to correlate with the amount of micrometastasis in each organ (FIG. 7E), implying that elevating HBB2 expression in the presence of micrometastasis is the host attempt to inhibit tumor progression.

Example 8. Treatment with HBB11p Inhibits Local Tumor Growth and Metastasis

Figure 8:
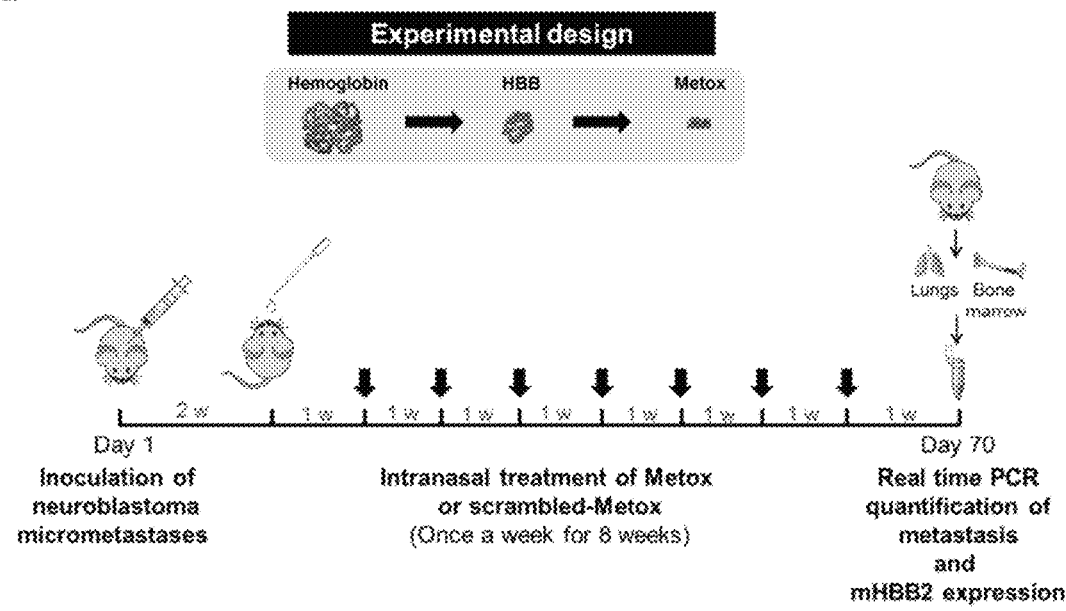
FIGS. 8A-8F. A short fragment of human HBB (Metox) inhibits neuroblastoma local tumor growth and metastasis.
Figure 8:
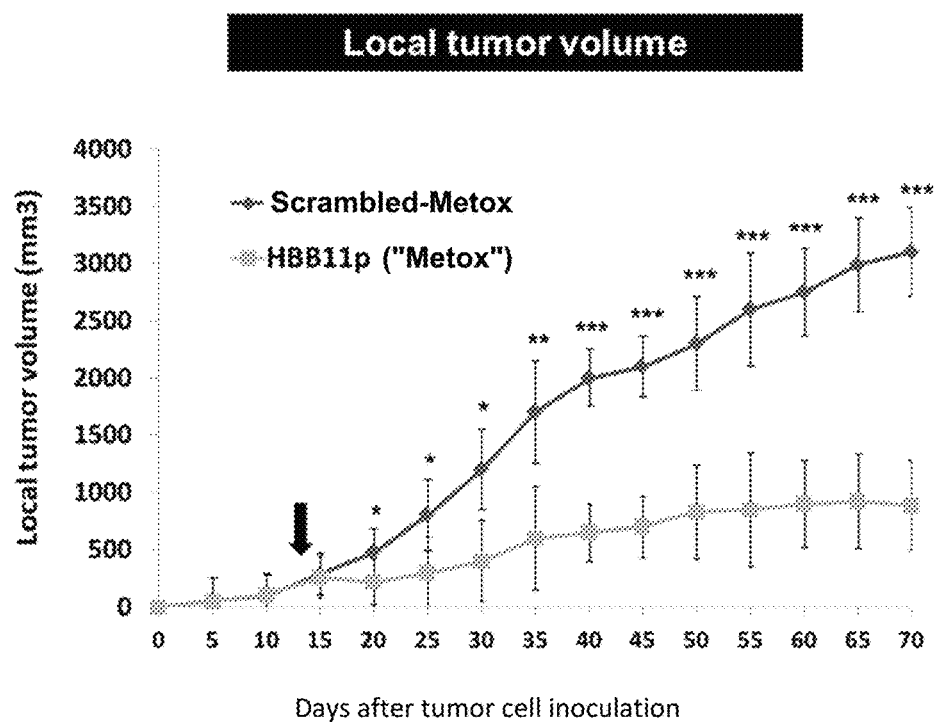

In an experiment similar to that described in Example 7, athymic nude mice were orthotopically inoculated with MicroNB cells to the adrenal gland. Fourteen days following inoculation, the mice were treated intranasally once a week for eight weeks with 1 mg/kg HBB11p ("Metox") or with the same amounts of a control peptide having the identical amino acid composition as Metox but in a scrambled sequence ("Scrambled-Metox") (FIG. 8A). Mice were monitored for tumor volume on a weekly basis.

Figure 8C:
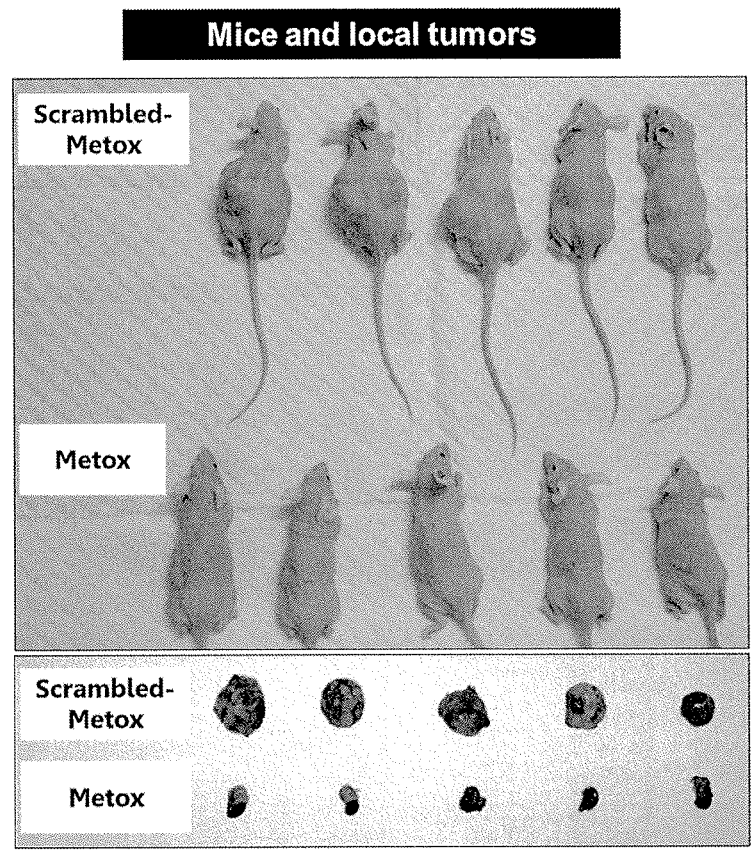
Figure 8D:
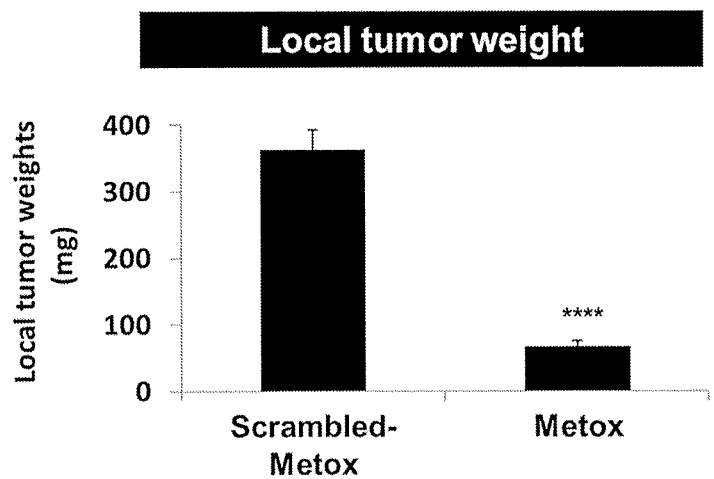

Twenty days after tumor cell inoculation a difference was apparent in local tumor volume between mice treated with Metox and mice treated with scrambled-Metox (FIG. 8B). This difference became more significant with time (FIG. 8B). Mice were euthanized 70 days post tumor cell inoculation and the resected local adrenal tumors were weighed. The weight of local tumors resected from scrambled-Metox treated mice was significantly higher than that of local adrenal tumors resected from mice treated intranasally with Metox (FIG. 8C, 8D).

Figure 8E:
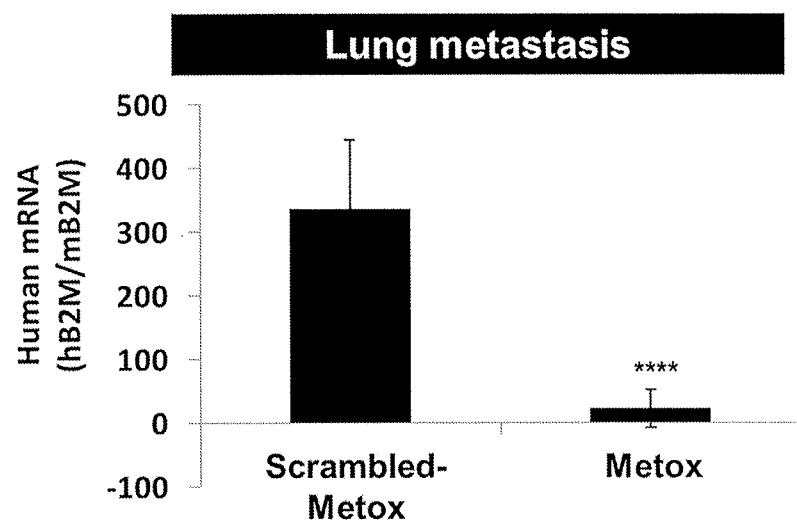
Figure 8F:
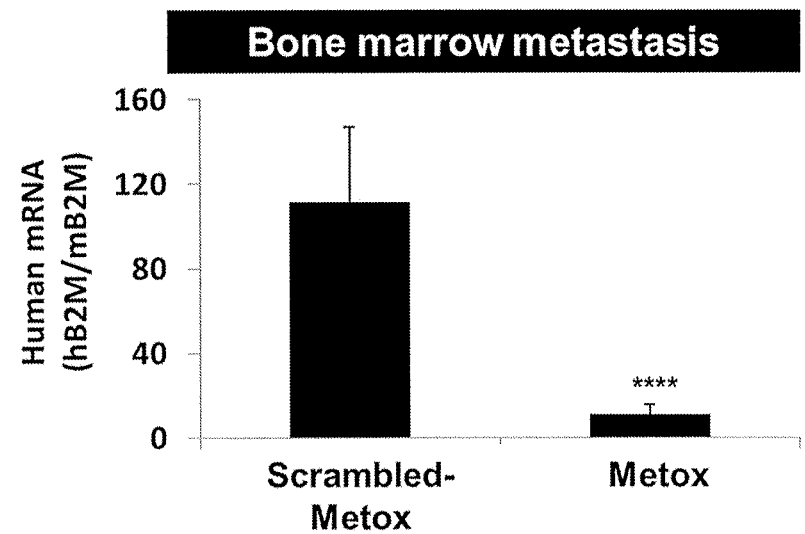

Mouse lungs and bone marrow were harvested and assayed by Real-Time PCR for the presence of human MicroNB cells. The metastatic load of MicroNB cells was significantly lower in lungs and bone marrow of mice treated with Metox compared to that found in organs derived from mice treated with scrambled-Metox (FIG. 8E, 8F).

REFERENCES

Aguirre-Ghiso, J. A. 2007. Models, mechanisms and clinical evidence for cancer dormancy. Nat Rev Cancer 7:834-846.

Biedler, J. L., S. Roffler-Tarlov, M. Schachner, and L. S. Freedman. 1978. Multiple neurotransmitter synthesis by human neuroblastoma cell lines and clones. Cancer Res 38:3751-3757.

Chambers, A. F., A. C. Groom, and I. C. MacDonald. 2002. Dissemination and growth of cancer cells in metastatic sites. Nat Rev Cancer 2:563-572.

Cowie, F., R. Corbett, and C. R. Pinkerton. 1997. Lung involvement in neuroblastoma: incidence and characteristics. Med Pediatr Oncol 28:429-432.

Edry Botzer, L., S. Maman, O. Sagi-Assif, T. Meshel, I. Nevo, T. Bauerle, I. Yron, and I. P. Witz. 2011. Lung-residing metastatic and dormant neuroblastoma cells. Am J Pathol 179:524-536.

Gupta, G. P., and J. Massague. 2006. Cancer metastasis: building a framework. Cell 127:679-695.

Holmgren, L., M. S. O'Reilly, and J. Folkman. 1995. Dormancy of micrometastases: balanced proliferation and apoptosis in the presence of angiogenesis suppression. Nat Med 1:149-153.

Ishikawa, N., S. Ohlmeier, K. Salmenkivi, M. Myllarniemi, I. Rahman, W. Mazur, and V. L. Kinnula. 2010. Hemoglobin alpha and beta are ubiquitous in the human lung, decline in idiopathic pulmonary fibrosis but not in COPD. Respiratory research 11:123.

Joyce, J. A., and J. W. Pollard. 2009. Microenvironmental regulation of metastasis. Nat Rev Cancer 9:239-252.

Kim, Y., M. A. Stolarska, and H. G. Othmer. 2011. The role of the microenvironment in tumor growth and invasion. Prog Biophys Mol Biol 106:353-379.

Klein-Goldberg, A., S. Maman, and I. P. Witz. 2014. The role played by the microenvironment in site-specific metastasis. Cancer Lett 352:54-58.

Maman, S., L. Edry-Botzer, O. Sagi-Assif, T. Meshel, W. Yuan, W. Lu, and I. P. Witz. 2013. The metastatic microenvironment: lung-derived factors control the viability of neuroblastoma lung metastasis. Int J Cancer 133:2296-2306.

Maman, S., and I. P. Witz. 2013b. The metastatic microenvironment. In The Tumor Immunoenvironment. M. R. Shurin, V. Umansky, and A. Malyguine, editors. Springer, N.Y, 745.

Merrifield, R. B. 1963. Solid Phase Peptide Synthesis. I. The Synthesis of a Tetrapeptide. Journal of the American Chemical Society 85:2149-2154.

Nevo, I., O. Sagi-Assif, L. Edry Botzer, D. Amar, S. Maman, N. Kariv, L. E. Leider-Trejo, L. Savelyeva, M. Schwab, I. Yron, and I. P. Witz. 2008. Generation and characterization of novel local and metastatic human neuroblastoma variants. Neoplasia 10:816-827.

Paez, D., M. J. Labonte, P. Bohanes, W. Zhang, L. Benhanim, Y. Ning, T. Wakatsuki, F. Loupakis, and H. J. Lenz. 2012. Cancer dormancy: a model of early dissemination and late cancer recurrence. Clin Cancer Res 18:645-653.

Pantel, K., and C. Alix-Panabieres. 2007. The clinical significance of circulating tumor cells. Nat Clin Pract Oncol 4:62-63.

Pantel, K., and R. H. Brakenhoff. 2004. Dissecting the metastatic cascade. Nat Rev Cancer 4:448-456.

Pietsch, T., E. Gottert, E. Meese, N. Blin, H. J. Feickert, H. Riehm, and G. Kovacs. 1988. Characterization of a continuous cell line (MHH-NB-11) derived from advanced neuroblastoma. Anticancer Res 8:1329-1333.

Rosenfeld, J., J. Capdevielle, J. C. Guillemot, and P. Ferrara. 1992. In-gel digestion of proteins for internal sequence analysis after one- or two-dimensional gel electrophoresis. Analytical biochemistry 203:173-179.

Schnolzer, M., P. Alewood, A. Jones, D. Alewood, and S. B. Kent. 1992. In situ neutralization in Boc-chemistry solid phase peptide synthesis. Rapid, high yield assembly of difficult sequences. International journal of peptide and protein research 40:180-193.

Smith, M. A., N. L. Seibel, S. F. Altekruse, L. A. Ries, D. L. Melbert, M. O'Leary, F. O. Smith, and G. H. Reaman. 2010. Outcomes for children and adolescents with cancer: challenges for the twenty-first century. J Clin Oncol 28:2625-2634.

Tomayko, M. M., and C. P. Reynolds. 1989. Determination of subcutaneous tumor size in athymic (nude) mice. Cancer chemotherapy and pharmacology 24:148-154.

Townson, J. L., and A. F. Chambers. 2006. Dormancy of solitary metastatic cells. Cell Cycle 5:1744-1750.

Wikman, H., R. Vessella, and K. Pantel. 2008. Cancer micrometastasis and tumour dormancy. APMIS: acta pathologica, microbiologica, et immunologica Scandinavica 116:754-770.

Witz, I. P. 2008a. Tumor-microenvironment interactions: dangerous liaisons. Adv Cancer Res 100:203-229.

Witz, I. P. 2008b. Yin-yang activities and vicious cycles in the tumor microenvironment. Cancer Res 68:9-13.

Witz, I. P., and O. Levy-Nissenbaum. 2006. The tumor microenvironment in the post-PAGET era. Cancer letters 242:1-10.

What is claimed is:

1. A method of treating a subject having cancer comprising administering an effective amount of a hemoglobin beta subunit (HBB) peptide to a subject having cancer, wherein the HBB peptide is a peptide consisting the amino acid sequence ENFRLLGNVLVCVLA, termed HBB11p (SEQ ID NO:5), or a functional variant of HBB11p having three or fewer amino acid changes.

2. The method of claim 1, wherein the cancer is selected from the group consisting of breast, cervical, colon, kidney, lung, skin, ovarian, pancreatic, prostate, rectal, stomach, thyroid, cervical, and uterine cancer, and a cancer of the nervous system.

3. The method of claim 1, wherein the cancer is neuroblastoma.

4. A method of inhibiting development of cancer in a subject at risk of developing cancer comprising administering an effective amount of a HBB peptide to a subject at risk of developing cancer, wherein the HBB peptide is a peptide consisting of the amino acid sequence ENFRLLGNVLVCVLA, termed HBB11p (SEQ ID NO:5), or a functional variant of HBB11p having three or fewer amino acid changes.

5. The method of claim 4, wherein the cancer is selected from the group consisting of breast, cervical, colon, kidney, lung, skin, ovarian, pancreatic, prostate, rectal, stomach, thyroid, cervical, and uterine cancer, and a cancer of the nervous system.

6. The method of claim 4, wherein the cancer is neuroblastoma.

7. The method of claim 4, wherein the subject at risk of developing cancer is a subject that was previously treated for cancer.

8. The method of claim 4, wherein the subject at risk of developing cancer is a subject in which cancer was previously cured.

9. A method of inhibiting metastasis of cancer in a subject having cancer comprising administering an effective amount of a HBB peptide to a subject having cancer, wherein the HBB peptide is a peptide consisting of the amino acid sequence ENFRLLGNVLVCVLA, termed HBB11p (SEQ ID NO:5), or a functional variant of HBB11p having three or fewer amino acid changes.

10. The method of claim 9, wherein the cancer is selected from the group consisting of breast, cervical, colon, kidney, lung, skin, ovarian, pancreatic, prostate, rectal, stomach, thyroid, cervical, and uterine cancer, and a cancer of the nervous system.

11. The method of claim 9, wherein the cancer is neuroblastoma.

12. A pharmaceutical composition comprising one or more HBB peptides and a pharmaceutically acceptable carrier, wherein the HBB peptide is a peptide consisting of the amino acid sequence ENFRLLGNVLVCVLA, termed HBB11p (SEQ ID NO:5), or a functional variant of HBB11p having three or fewer amino acid changes.

13. A peptide consisting of the amino acid sequence ENFRLLGNVLVCVLA, termed HBB11p (SEQ ID NO:5), or a functional variant of HBB11p having one or fewer amino acid changes.

14. The method of claim 2, wherein the skin cancer is melanoma.

15. The method of claim 5, wherein the skin cancer is melanoma.

16. The method of claim 10, wherein the skin cancer is melanoma.

* * * * *

SEQUENCE LISTING

```
<160> NUMBER OF SEQ ID NOS: 29

<210> SEQ ID NO 1
<211> LENGTH: 147
<212> TYPE: PRT
<213> ORGANISM: Mus musculus

<400> SEQUENCE: 1

Met Val His Leu Thr Asp Ala Glu Lys Ser Ala Val Ser Cys Leu Trp
1               5                   10                  15

Ala Lys Val Asn Pro Asp Glu Val Gly Gly Glu Ala Leu Gly Arg Leu
            20                  25                  30

Leu Val Val Tyr Pro Trp Thr Gln Arg Tyr Phe Asp Ser Phe Gly Asp
        35                  40                  45

Leu Ser Ser Ala Ser Ala Ile Met Gly Asn Pro Lys Val Lys Ala His
    50                  55                  60

Gly Lys Lys Val Ile Thr Ala Phe Asn Glu Gly Leu Lys Asn Leu Asp
65                  70                  75                  80

Asn Leu Lys Gly Thr Phe Ala Ser Leu Ser Glu Leu His Cys Asp Lys
                85                  90                  95

Leu His Val Asp Pro Glu Asn Phe Arg Leu Leu Gly Asn Ala Ile Val
            100                 105                 110

Ile Val Leu Gly His His Leu Gly Lys Asp Phe Thr Pro Ala Ala Gln
        115                 120                 125

Ala Ala Phe Gln Lys Val Val Ala Gly Val Ala Thr Ala Leu Ala His
    130                 135                 140

Lys Tyr His
145

<210> SEQ ID NO 2
<211> LENGTH: 147
<212> TYPE: PRT
<213> ORGANISM: Homo sapiens

<400> SEQUENCE: 2

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80
```

```
Asn Leu Lys Gly Thr Phe Ala Thr Leu Ser Glu Leu His Cys Asp Lys
                85                  90                  95
Leu His Val Asp Pro Glu Asn Phe Arg Leu Leu Gly Asn Val Leu Val
            100                 105                 110
Cys Val Leu Ala His His Phe Gly Lys Glu Phe Thr Pro Pro Val Gln
        115                 120                 125
Ala Ala Tyr Gln Lys Val Val Ala Gly Val Ala Asn Ala Leu Ala His
    130                 135                 140
Lys Tyr His
145

<210> SEQ ID NO 3
<211> LENGTH: 55
<212> TYPE: PRT
<213> ORGANISM: Homo sapiens

<400> SEQUENCE: 3

Val His Leu Thr Pro Glu Glu Lys Ser Ala Val Thr Ala Leu Trp Gly
1               5                   10                  15
Lys Val Asn Val Asp Glu Val Gly Gly Glu Ala Leu Gly Arg Leu Leu
            20                  25                  30
Val Val Tyr Pro Trp Thr Gln Arg Phe Phe Glu Ser Phe Gly Asp Leu
        35                  40                  45
Ser Thr Pro Asp Ala Val Met
    50                  55

<210> SEQ ID NO 4
<211> LENGTH: 91
<212> TYPE: PRT
<213> ORGANISM: Homo sapiens

<400> SEQUENCE: 4

Gly Asn Pro Lys Val Lys Ala His Gly Lys Lys Val Leu Gly Ala Phe
1               5                   10                  15
Ser Asp Gly Leu Ala His Leu Asp Asn Leu Lys Gly Thr Phe Ala Thr
            20                  25                  30
Leu Ser Glu Leu His Cys Asp Lys Leu His Val Asp Pro Glu Asn Phe
        35                  40                  45
Arg Leu Leu Gly Asn Val Leu Val Cys Val Leu Ala His His Phe Gly
    50                  55                  60
Lys Glu Phe Thr Pro Pro Val Gln Ala Ala Tyr Gln Lys Val Val Ala
65                  70                  75                  80
Gly Val Ala Asn Ala Leu Ala His Lys Tyr His
                85                  90

<210> SEQ ID NO 5
<211> LENGTH: 15
<212> TYPE: PRT
<213> ORGANISM: Homo sapiens

<400> SEQUENCE: 5

Glu Asn Phe Arg Leu Leu Gly Asn Val Leu Val Cys Val Leu Ala
1               5                   10                  15

<210> SEQ ID NO 6
<211> LENGTH: 15
<212> TYPE: PRT
<213> ORGANISM: Artificial Sequence
<220> FEATURE:
```

<223> OTHER INFORMATION: HBBp11 scrambled peptide sequence

<400> SEQUENCE: 6

Ala Asn Val Leu Asn Glu Cys Val Phe Val Gly Arg Leu Leu Leu
1               5                   10                  15

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
atgtaagcag catcatggag                                          20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
aagcaagcag aatttggaat                                          20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
ctggtctttc tggtgcttgt                                          20

<210> SEQ ID NO 10
<211> LENGTH: 24
<212> TYPE: DNA
<213> ORGANISM: Artificial Sequence
<220> FEATURE:
<223> OTHER INFORMATION: PCR primer

<400> SEQUENCE: 10
ggcgtgagta tacttgaatt tgag                                     24

<210> SEQ ID NO 11
<211> LENGTH: 19
<212> TYPE: DNA
<213> ORGANISM: Artificial Sequence
<220> FEATURE:
<223> OTHER INFORMATION: PCR primer

<400> SEQUENCE: 11
ctatcctgvv vacgtgtga                                           19

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
cttgatggtc ttagattccg g                                        21

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
ggccgcgttc ttccatttgt                                              20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
gatttcgcat ttcgtcatgc                                              20

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
gtgacaagct gcatgtggat                                              20

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
aggtggtggc ccagcacaat                                              20

<210> SEQ ID NO 17
<211> LENGTH: 15
<212> TYPE: PRT
<213> ORGANISM: Homo sapiens

<400> SEQUENCE: 17

Val His Leu Thr Pro Glu Glu Lys Ser Ala Val Thr Ala Leu Trp
1               5                  10                  15

<210> SEQ ID NO 18
<211> LENGTH: 15
<212> TYPE: PRT
<213> ORGANISM: Homo sapiens

<400> SEQUENCE: 18

Val Thr Ala Leu Trp Gly Lys Val Asn Val Asp Glu Val Gly Gly
1               5                  10                  15

<210> SEQ ID NO 19
<211> LENGTH: 15
<212> TYPE: PRT
<213> ORGANISM: Homo sapiens

<400> SEQUENCE: 19

Asp Glu Val Gly Gly Glu Ala Leu Gly Arg Leu Leu Val Val Tyr

<210> SEQ ID NO 20
<211> LENGTH: 15
<212> TYPE: PRT
<213> ORGANISM: Homo sapiens

<400> SEQUENCE: 20

Leu Leu Val Val Tyr Pro Trp Thr Gln Arg Phe Phe Glu Ser Phe
1               5                   10                  15

<210> SEQ ID NO 21
<211> LENGTH: 15
<212> TYPE: PRT
<213> ORGANISM: Homo sapiens

<400> SEQUENCE: 21

Phe Phe Glu Ser Phe Gly Asp Leu Ser Thr Pro Asp Ala Val Met
1               5                   10                  15

<210> SEQ ID NO 22
<211> LENGTH: 15
<212> TYPE: PRT
<213> ORGANISM: Homo sapiens

<400> SEQUENCE: 22

Pro Asp Ala Val Met Gly Asn Pro Lys Val Lys Ala His Gly Lys
1               5                   10                  15

<210> SEQ ID NO 23
<211> LENGTH: 15
<212> TYPE: PRT
<213> ORGANISM: Homo sapiens

<400> SEQUENCE: 23

Lys Ala His Gly Lys Lys Val Leu Gly Ala Phe Ser Asp Gly Leu
1               5                   10                  15

<210> SEQ ID NO 24
<211> LENGTH: 15
<212> TYPE: PRT
<213> ORGANISM: Homo sapiens

<400> SEQUENCE: 24

Phe Ser Asp Gly Leu Ala His Leu Asp Asn Leu Lys Gly Thr Phe
1               5                   10                  15

<210> SEQ ID NO 25
<211> LENGTH: 15
<212> TYPE: PRT
<213> ORGANISM: Homo sapiens

<400> SEQUENCE: 25

Leu Lys Gly Thr Phe Ala Thr Leu Ser Glu Leu His Cys Asp Lys
1               5                   10                  15

<210> SEQ ID NO 26
<211> LENGTH: 15
<212> TYPE: PRT
<213> ORGANISM: Homo sapiens

<400> SEQUENCE: 26

Leu His Cys Asp Lys Leu His Val Asp Pro Glu Asn Phe Arg Leu
1               5                   10                  15

```
<210> SEQ ID NO 27
<211> LENGTH: 15
<212> TYPE: PRT
<213> ORGANISM: Homo sapiens

<400> SEQUENCE: 27

Val Cys Val Leu Ala His His Phe Gly Lys Glu Phe Thr Pro Pro
1               5                   10                  15

<210> SEQ ID NO 28
<211> LENGTH: 15
<212> TYPE: PRT
<213> ORGANISM: Homo sapiens

<400> SEQUENCE: 28

Glu Phe Thr Pro Pro Val Gln Ala Ala Tyr Gln Lys Val Val Ala
1               5                   10                  15

<210> SEQ ID NO 29
<211> LENGTH: 16
<212> TYPE: PRT
<213> ORGANISM: Homo sapiens

<400> SEQUENCE: 29

Gln Lys Val Val Ala Gly Val Ala Asn Ala Leu Ala His Lys Tyr His
1               5                   10                  15
```